(12) United States Patent
Milgram et al.

(10) Patent No.: US 7,884,318 B2
(45) Date of Patent: Feb. 8, 2011

(54) SYSTEMS, METHODS, AND COMPUTER-READABLE MEDIUM FOR DETERMINING COMPOSITION OF CHEMICAL CONSTITUENTS IN A COMPLEX MIXTURE

(75) Inventors: K. Eric Milgram, Limerick, PA (US);
Thomas Barrett, Raleigh, NC (US);
Anne M Evans, Durham, NC (US)

(73) Assignee: Metabolon, Inc., Durham, NC (US)

( * ) Notice: Subject to any disclaimer, the term of this patent is extended or adjusted under 35 U.S.C. 154(b) by 227 days.

(21) Appl. No.: 12/327,758

(22) Filed: Dec. 3, 2008

(65) Prior Publication Data

US 2009/0179147 A1    Jul. 16, 2009

Related U.S. Application Data

(60) Provisional application No. 61/021,508, filed on Jan. 16, 2008, provisional application No. 61/114,869, filed on Nov. 14, 2008.

(51) Int. Cl.
*B01D 59/44* (2006.01)
*H01J 49/00* (2006.01)

(52) U.S. Cl. .................. 250/282; 250/281; 702/19; 702/22; 702/23; 435/7; 435/7.21; 435/4; 435/6; 435/25; 435/49; 435/320.1

(58) Field of Classification Search ............... 250/281, 250/282; 702/19, 22, 23; 435/7, 7.21, 4, 435/6, 25, 49, 320.1
See application file for complete search history.

(56) References Cited

U.S. PATENT DOCUMENTS

2006/0200316 A1 *  9/2006  Kanani et al. ............. 702/19

(Continued)

FOREIGN PATENT DOCUMENTS

JP    06-102250 A    4/1994

(Continued)

OTHER PUBLICATIONS

Notification of Transmittal of the International Search Report and the Written Opinion of the International Searching Authority, or the Declaration for International Application No. PCT/US2009/031168 (Aug. 19, 2009).

*Primary Examiner*—Jack I Berman
*Assistant Examiner*—Meenakshi S Sahu
(74) *Attorney, Agent, or Firm*—Jenkins, Wilson, Taylor & Hunt, P.A.

(57) ABSTRACT

Systems, methods, and computer-readable media for determining composition of chemical constituents in a complex mixture are disclosed. According to one aspect, a method for determining composition of chemical constituents in a complex mixture includes generating, using a separation tool and a mass spectrometer, separation and mass spectrometry data of a sample, wherein the separation data includes peak information and wherein the mass spectrometry data includes primary and secondary mass spectrometry data. The analysis results, including the generated separation and mass spectrometry data, are collected and stored. A chemical constituent of the sample is determined by comparing the analysis results to a library of information indicating characteristics of chemical entities, where the comparison is based on the separation and mass spectrometry information. The library of information includes data generated by the separation tool and mass spectrometer, and also includes separation and mass spectrometry data for both identified and unidentified chemical entities. An indication of the chemical constituent of the sample is made available in human-accessible form.

45 Claims, 33 Drawing Sheets

U.S. PATENT DOCUMENTS

2007/0059770 A1* 3/2007 Anderson et al. ............ 435/7.1
2008/0234948 A1* 9/2008 Walk et al. .................... 702/23

FOREIGN PATENT DOCUMENTS

| | | |
|---|---|---|
| JP | 10-019868 A | 1/1998 |
| JP | 13-165922 A | 6/2001 |
| JP | 17-315704 A | 11/2005 |
| WO | WO 2009/091933 A2 | 7/2009 |

* cited by examiner

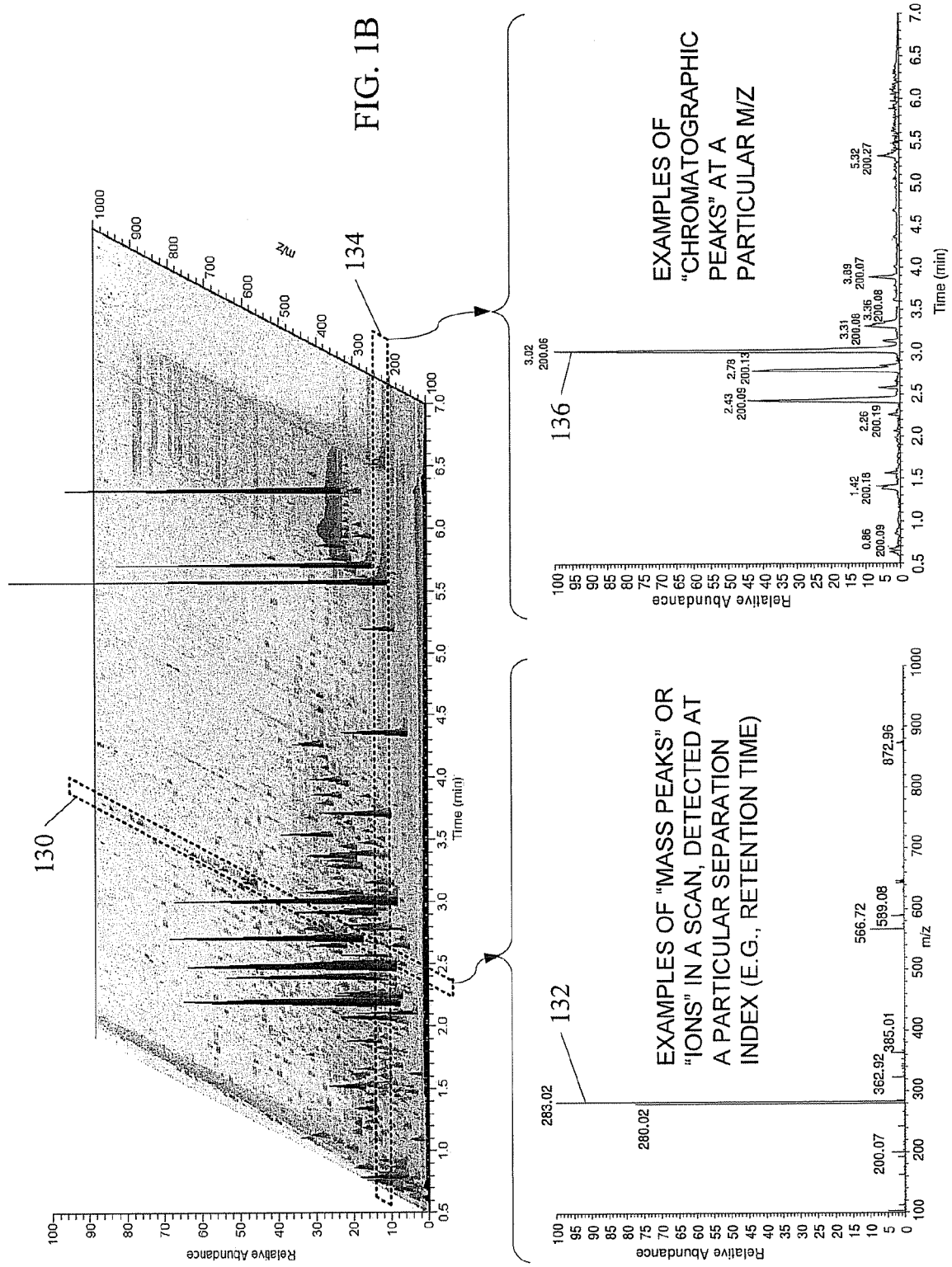

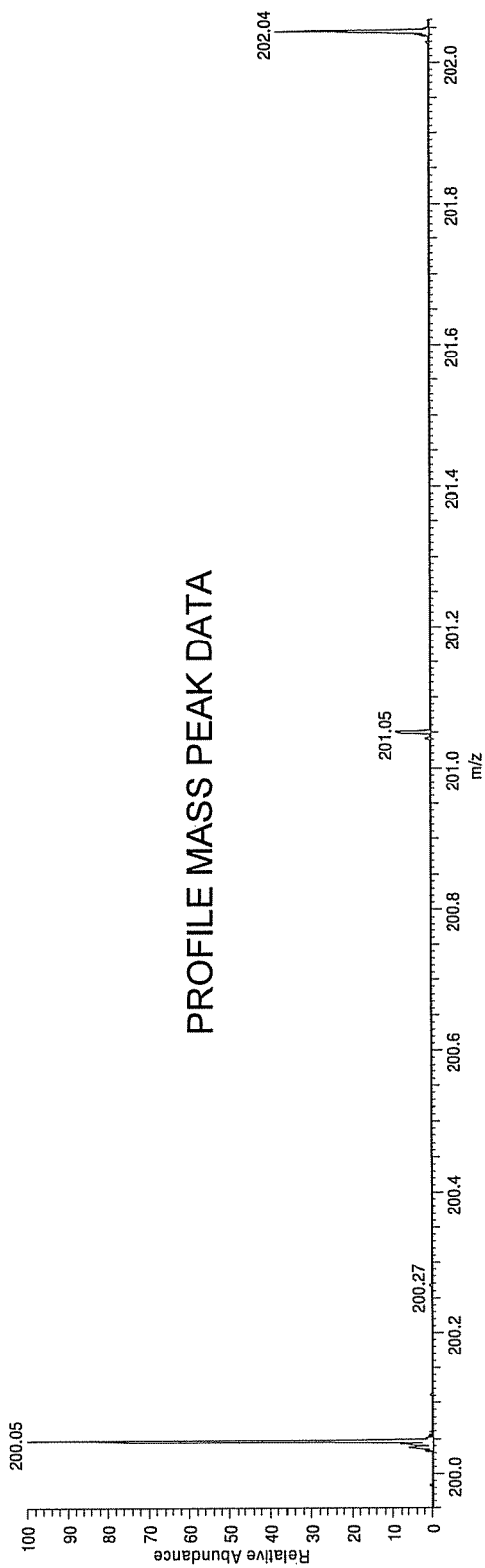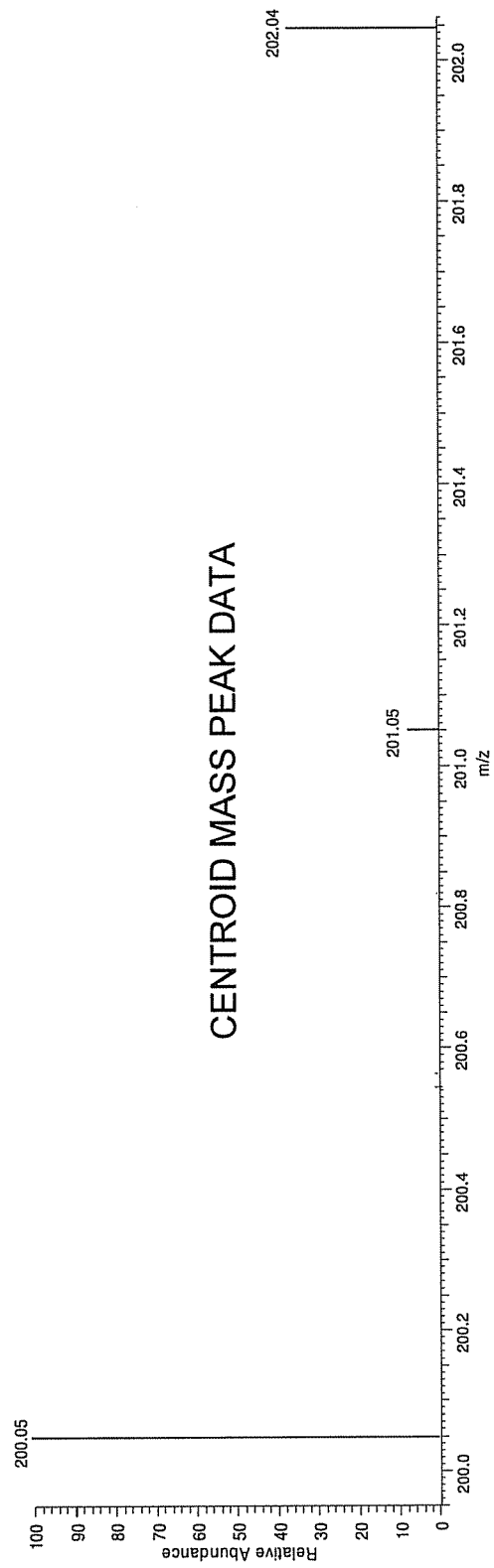
FIG. 1C

```
TABLE MBZR_SCANS
    SCAN_ID              PRIMARY KEY FOR RECORD
    TASK_ID              TASK ID
    SCAN_NUMBER          SCAN NUMBER
    RT                   RETENTION TIME IN MINUTES
    RI                   RETENTION INDEX
    FILTER               RAW INSTRUMENT FILTER
    DATA_STREAM          DATA STREAM
    SCAN_LEVEL           1=PRIMARY SCAN, 2>MS/MS
    MASS_RANGE_LOW       LOW MASS SCANNED
    MASS_RANGE_HIGH      HIGH MASS SCANNED
    NUMB_POINTS          NUMBER OF MASS, INTENSITY POINTS STORED IN POINTS
    POINTS               TEXT REPRESENTATION OF MASS, INTENSITY PAIRS ON MASS ORDER
    ACTUAL_SCAN_NUMBER   ACTUAL INCREMENTAL SCAN NUMBER
```

FIG.2A

```
TABLE CHRO_ION_TREES
    TASK_ID              TASK ID
    NODE_ID              PRIMARY KEY OF NODE
    PARENT_NODE_ID       PARENT NODE
    MASS                 MASS OF LINKING ION
    RT                   RETENTION TIME IN MINUTES
    RI                   RETENTION INDEX
    SCAN_ID              REFERENCE TO SCAN DATA
```

FIG.2B

TABLE MBZR_PEAK
PEAK_ID
COMPONENT_ID
TEST_ID
COMPONENT_INDEX
APEX_SCAN
APEX_RT
RI
HEIGHT
NOISE
WIDTH_RT
WIDTH_SCAN
WIDTH_HALF_HEIGHT
AREA
SYMMETRY
MASS
INTENSITY
START_SCAN
START_RT
START_INTENSITY
END_SCAN
END_RT
END_INTENSITY
VERSION
STATUS
DATA_STREAM
SELECTED
LIB_IDENTIFIED

FIG.2C

TABLE MBZR_COMPONENT
COMPONENT_ID
TEST_ID
COMPONENT_INDEX
APEX_RT
START_RT
END_RT
HEIGHT
AREA
BASEPEAK_MASS
NOISE
RI
WIDTH_RT
SYMMETRY
PURITY
APEX_SCAN
START_SCAN
END_SCAN
REFERENCE_ID
NUM_PEAKS
STATUS
VERSION

FIG.2D

```
TABLE CHRO_LIB_ENTRY
    LIB_ID                  LIBRARY ID;
    COMP_ID                 COMPONENT ID;
    COMP_ID_SET             COMPONENT ID SET - LINKS MULT ENTRIES;
    RT                      RETENTION TIME IN MINUTES;
    RT_WINDOW               RETENTION TIME WINDOW IN MINUTES;
    RI                      RETENTION INDEX;
    RI_WINDOW               RETENTION INDEX WINDOW;
    CHEMICAL_ID             LINK TO LIMSUSER.CHEMICAL TABLE;
    EXP_FUNCTION            I = IGNORE, S = SUM, A = AVERAGE;
    QUANT_STD               QUANTITATION STANDARD;
    RI_LADDER               RETENTION LADDER;
    RECOVERY_CHECK          RECOVERY_CHECK (Y/NULL);
    DERIV_CHECK             DERIV_CHECK;
    MATRIX_CHECK            MATRIX_CHECK;
    ORIGIN                  HAND LOADED, CLUSTER, SINGLE COMPONENT;
    TASK_ID                 TEST ID OF SINGLE COMPONENT;
    COMPONENT_INDEX         COMPONENT INDEX OF SINGLE COMPONENT;
    GROUP_NAME              GROUP NAME FROM PEAK_CLUSTER;
    CLUSTER_NUMBER          CLUSTER NUMBER FROM PEAK_CLUSTER;
    RESPONSE_NORM_ORDER     RESPONSE NORMALIZATION ORDER;
    RESPONSE_NORM_FACTOR    RESPONSE NORMALIZATION FACTOR ;
    DISPLAY_COLOR           NAME OR RBG CODE OF COLOR USED IN DISPLAY;
    COMP_ID_ALT             ALTERNATE COMPONENT ID;
    TARGET_MASS             MASS ASSOCIATED WITH THE IONS IN THE COMPONENT;
    POS_NEG_FACTOR          RATIO OF POS AREA / NEG AREA ;
    QUANT_STREAM            BEST STREAM TO QUANT (POS/NEG HIGH AND LOW;
    TIMESTAMP               LAST CHANGED;
    TARGET_MASS_WINDOW      +/- MASS;
    COMMENTS                GENERAL COMMENTS;
    MIN_QUANT_AREA          USED TO FILTER LOW LEVEL IONS FROM CONSIDERATION;
```

FIG.2E

```
TABLE CHRO_LIB_MASSES
    COMP_ID                COMPONENT ID;
    LIB_ID                 LIBRARY ID;
    MASS                   MASS OF ION IN AMU;
    MASS_WINDOW            MASS WINDOW IN AMU;
    MASS_RATIO             RATIO TO PRIMARY ION IN PERCENT;
    MASS_NORMALIZER        Y = DIVISOR IN MASS RATIO;
    QUANT_MASS             Y = MASS USED TO DETERMINE COMPONENT RESPONSE OR QUANTITY;
    WEIGHTING              WEIGHT TO ASSIGN TO A MATCHED ION;
    DATA_STREAM            IDENTIFIES DATA STREAM IN WHICH THE MASS WAS FOUND;
    NAME                   USED IN LC TO ID IONS BASED ON MASS, CHARGE, AND ISOTOPE;
    TIMESTAMP              LAST CHANGED;
    CHRO_LIB_MASSES_ID     PRIMARY KEY;
    PARENT_ID              POINTS TO PARENT ION IN HIGH ORDER MS DATA;
```

Panel 422:
- Compound Name: (+)-catechin
- Library ID: 200
- Compound ID: 17668
- Chemical Report Name:
- Set Compound Name: (+)-catechin
- Library Report Name:
- Chemical Name: (+)-catechin
- Chemical Details | Upload Formula Panel 424:
- Status: silver
- Cluster Number:
- Exp. Function: Sum
- Group Name: Task Group [lc plex 103 pos]
- Display Color: Blue
- Origin: IonTracker
- Pos/Neg Factor: 0
- Min Quant Area:
- Target Mass: 290.10 ±
- Confidence: 100
- Comment: RI adjusted
- RT: 2.42   RT Window: 2
- RI: 2493   RI Window: 25
- Recovery Check: ○ Yes  ○ No
- Derivitization Check: ○ Und  ○ Der
- Matrix Check: ○ Yes  ○ No
- Quant Standard: ○ Yes  ○ No
- Quant Stream: ● [+]  ○ [−]

| Mass | Public DB | | | | | | | |
|---|---|---|---|---|---|---|---|---|
| | MASS | MASS_WIND... | MASS_RATIO | MASS_NORM... | QUANT_MASS | WEIGHTING | DATA_STRE... | NAME |
| | 139.2 | 0.4 | 100 | Y | | 0.38 | +i | M-151 |
| | 289.2 | 0.4 | 100 | Y | | 2.1602 | +i | M-1 |
| | 291.1 | 0.4 | 100 | Y | 1 | 72.2872 | +i | m+H |
| | 292.1 | 0.4 | 15.6 | | | 11.3011 | +i | m+H[C13-1] |
| | 293.1 | 0.4 | 2.3 | | | 1.6902 | +i | m+H[C13-2] |
| | 306 | 0.4 | 100 | Y | | 5.3605 | +i | M+16 |
| | 307 | 0.4 | 11 | | | 0.7801 | +i | M+16[C13-1] |

| MASS | MASS_WIND... | MASS_RATIO | MASS_NORM... | QUANT_MASS | WEIGHTING | DATA_STRE... | NAME |
|---|---|---|---|---|---|---|---|
| 291.1 | 0.4 | 100 | Y | 1 | 72.2872 | +i | m+H |

| MASS | MASS_WINDOW | MASS_RATIO | MASS_NORMA... | QUANT_MASS | WEIGHTING | DATA_STREAM | NAME |
|---|---|---|---|---|---|---|---|
| 95.2 | 0.3 | 0.1 | | | 0.0059 | +i | |
| 105.2 | 0.3 | 0.2 | | | 0.0439 | +i | |
| 111.2 | 0.3 | 0.2 | | | 0.0464 | +i | |
| 119.2 | 0.3 | 0.5 | | | 0.1244 | +i | |
| 123.1 | 0.3 | 98.2 | | | 25.2276 | +i | |
| 124.1 | 0.3 | 2.3 | | | 0.5957 | +i | |
| 125.2 | 0.3 | 0.1 | | | 0.0261 | +i | |
| 127.1 | 0.3 | 0.6 | | | 0.1591 | +i | |
| 137.2 | 0.3 | 0.8 | | | 0.2291 | +i | |
| 139.1 | 0.3 | 100 | Y | | 29.0291 | +i | |
| 140.1 | 0.3 | 2.2 | | | 0.6432 | +i | |
| 147.1 | 0.3 | 8.7 | | | 2.6708 | +i | |
| 148.1 | 0.3 | 1 | | | 0.3091 | +i | |

FIG.4G

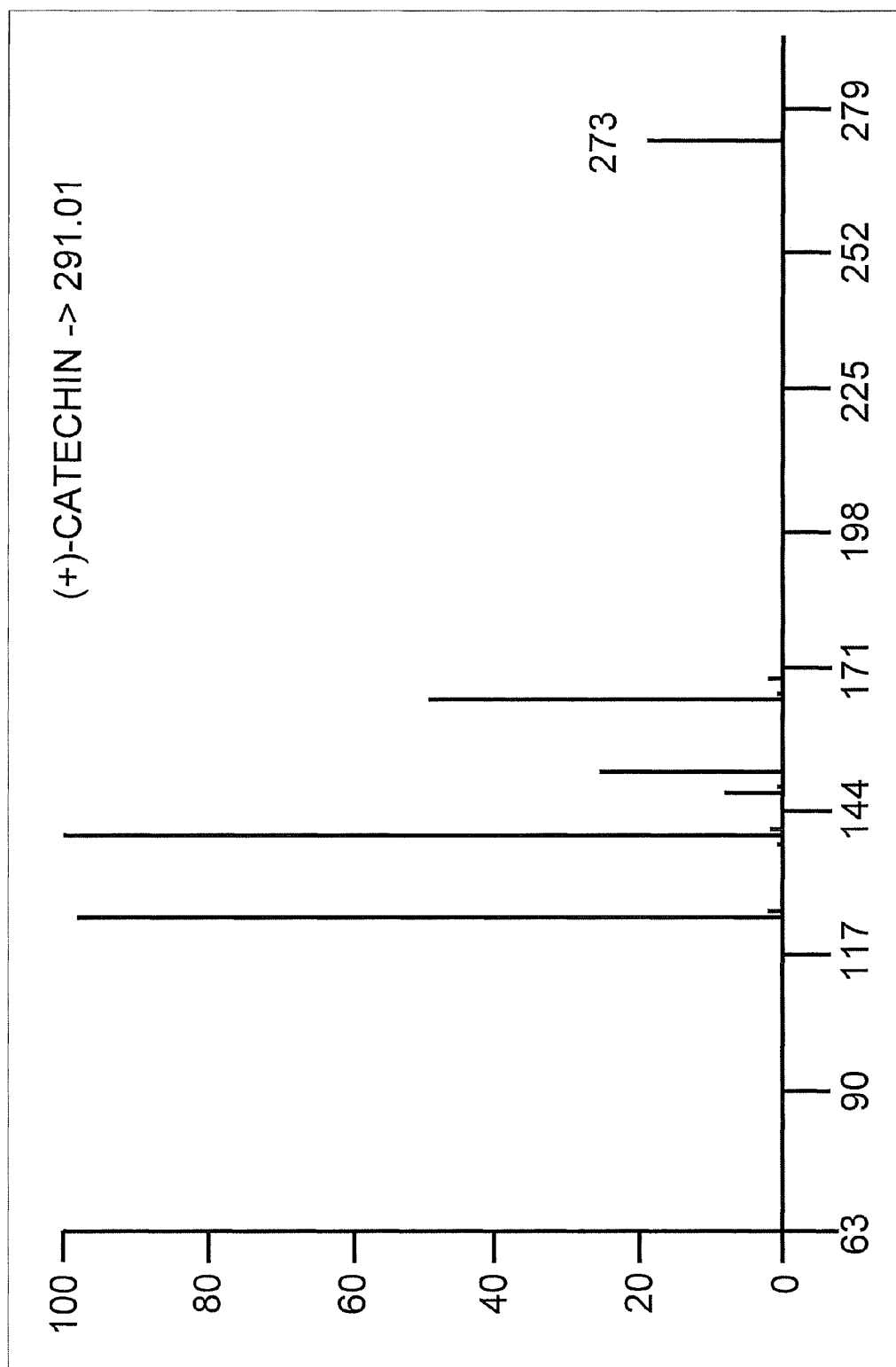

FIG.4K

General

- Chemical ID: 2068
- Chemical Name: (+)-catechin
- Parent Chemical:
- Description:
- IUPAC Name: (2R,3S)-2-(3,4-dihydroxyphenyl)ch
- Classification:
- CAS: 154-23-4

Physical

- State:
- Storage:
- Appearance:

Properties

- Boiling Point:
- Melting Point:
- Density:

Details

- Mol Formula: C15H14O6
- Mol Weight: 290.2680
- Exact_Mass: 290.0790381820
- SMILES: OC1=C[C@@]([C@@H](O2)[C@@H](O)CC3=C2C=C(O)C=C3O)=CC=C1O

430

Links

| Library | Public DB | | | | |
|---|---|---|---|---|---|
| Summary | Lib ID | Comp ID | Name | RI | QUANT |
| 50-\DSQ-\DSQ1- | 50 | 17668 | (+)-catechin | 2223.8 | |
| 59-\DSQ-\PLEX 2 | 59 | 17668 | (+)-catechin | 2223.8 | |
| 61-\LTQ-\V2.1-\ | 61 | 17668 | (+)-catechin | 9290 | |
| 62-\LTQ-\PLEX 2 | 62 | 17668 | (+)-catechin | 9290 | |
| 73-\LTQ-\plex 25 | 73 | 17668 | (+)-catechin | 1787 | |
| 185-\LTQ-\LCMS | 185 | 17668 | (+)-catechin | 2493 | |
| 186-\LTQ-\LCMS | 186 | 17668 | (+)-catechin | 2429 | |
| 200-\LTQ-\LCMS | 200 | 17668 | (+)-catechin | 2493 | |
| 201-\LTQ-\LCMS | 201 | 17668 | (+)-catechin | 2429 | |

OTHER DETAILS
438

| Stock | Annotation | Keywords | Attachments |
|---|---|---|---|

| SAMPLE_ID | NAME | AMOUNT | UNITS | PURITY | SUPPLIER |
|---|---|---|---|---|---|
| 58973 | Stock (+)-catec | 10.91 | mM | 100 | |
| 169128 | Stock (+)-catec | 1000 | mg | 96 | Fluka |

FIG.4P

| Sample Name | Acquired Date | File Name | Client ID | Client Name |
|---|---|---|---|---|
| CW-00057-LC-... | 10/12/2007 | LTQ2260711112P_NASH12... | | |
| CW-00042-LC-... | 10/12/2007 | LTQ2260711112P_NASH12_38.RAW | C05-16-... | Case Waste |
| CW-00054-LC-... | 10/13/2007 | LTQ2260711112P_NASH12_32.RAW | N05-16-... | Case Waste |
| CW-00055-LC-... | 10/13/2007 | LTQ2260711112P_NASH12_30.RAW | N05-16-... | Case Waste |
| CW-00047-LC-... | 10/13/2007 | LTQ2260711112P_NASH12_35.RAW | C05-16-... | Case Waste |
| CW-00052-LC-... | 10/13/2007 | LTQ2260711112P_NASH12_07.RAW | N05-172... | Case Waste |
| CW-00051-LC-... | 10/13/2007 | LTQ2260711112P_NASH12_45.RAW | C05-172... | Case Waste |
| CW-00041-LC-... | 10/13/2007 | LTQ2260711112P_NASH12_40.RAW | C05-16-... | Case Waste |
| CW-00045-LC-... | 10/13/2007 | LTQ2260711112P_NASH12_37.RAW | C05-16-... | Case Waste |
| CW-00071-LC-... | 10/13/2007 | LTQ2260711112P_NASH12_11.RAW | C05-16-... | Case Waste |
| CW-00053-LC-... | 10/13/2007 | LTQ2260711112P_NASH12_23.RAW | N05-172... | Case Waste |
| CW-00048-LC-... | 10/13/2007 | LTQ2260711112P_NASH12_18.RAW | C05-172... | Case Waste |
| CW-00068-LC-... | 10/13/2007 | LTQ2260711112P_NASH12_09.RAW | N05-172... | Case Waste |
| CW-00044-LC-... | 10/13/2007 | LTQ2260711112P_NASH12_29.RAW | C05-16-... | Case Waste |

FIG.4R

| RT | RI | Area |
|---|---|---|
| .58 | 574.54 | 22,415,714 |
| .64 | 633.11 | 13,628,034 |
| .68 | 676.84 | 21,568,821 |
| .76 | 764.52 | 51,381,566 |
| .79 | 793.06 | 3,690,855 |
| .84 | 842.56 | 38,777,339 |
| 1.04 | 1054.5 | 5,691,963 |
| 1.16 | 1177.8 | 8,056,277 |
| 1.21 | 1236.9 | 14,743,021 |

SYSTEMS, METHODS, AND COMPUTER-READABLE MEDIUM FOR DETERMINING COMPOSITION OF CHEMICAL CONSTITUENTS IN A COMPLEX MIXTURE

PRIORITY CLAIM

This application claims the benefit of U.S. Provisional Patent Application Ser. No. 61/021,508, filed Jan. 16, 2008, and U.S. Provisional Patent Application Ser. No. 61/114,869, filed Nov. 14, 2008, the disclosures of which are incorporated herein by reference in the entirety.

TECHNICAL FIELD

The subject matter described herein relates to systems and methods for determining composition of chemical constituents in a complex mixture.

BACKGROUND

The ability to determine the composition of chemical constituents in a complex mixture has a broad range of highly useful applications, including answering questions posed by traditional chemical analysis, such as "What is this substance made of?", and enabling more sophisticated analysis of biological processes, such as "How is a healthy cell different from a diseased cell?", "How does this medicine affect the cellular process?", "How can the growth of cells in culture be optimized?", and "What is the limiting factor for this bioprocess?".

The techniques traditionally used in analysis of complex mixtures include chromatography and mass spectrometry. Chromatography is a technique whereby a complex mixture is separated into parts. Mass spectrometry is a technique in which a sample containing many different chemical constituents is ionized, and the ionized chemical constituents are subjected to an electromagnetic field, which separates the chemical constituents according to their mass-to-charge (m/z) ratios. Although both chromatography and mass spectrometry separate a complex mixture into constituent parts, neither technique provides direct identification of the chemical constituents; the identity of a chemical constituent must be determined based on an analysis of the measured characteristics of the chemical constituent.

As used herein, the term "separation" refers to the process of separating a complex mixture into its component molecules or metabolites. Common laboratory separation techniques include electrophoresis and chromatography.

As used herein, the term "chromatography" refers to a physical method of separation in which the components (i.e., chemical constituents) to be separated are distributed between two phases, one of which is stationary (stationary phase) while the other (the mobile phase) moves in a definite direction. Chromatographic output data may be used for manipulation by embodiments of the subject matter described herein.

As used herein, the term "retention time", refers to the elapsed time in a chromatography process since the introduction of the sample into the separation device. The retention time of a constituent of a sample refers to the elapsed time in a chromatography process between the time of injection of the sample into the separation device and the time that the constituent of the sample elutes (e.g., exits from) the portion of the separation device that contains the stationary phase.

As used herein, the term "retention index" of a sample component refers to a number, obtained by interpolation (usually logarithmic), relating the retention time or the retention factor of the sample component to the retention times of standards eluted before and after the peak of the sample component, a mechanism that uses the separation characteristics of known standards to remove systematic error.

As used herein, the term "separation index" refers to a metric associated with chemical constituents separated by a separation technique. For chromatographic separation techniques, the separation index may be retention time or retention index. For non-chromatographic separation techniques, the separation index may be physical distance traveled by the chemical constituent.

As used herein, the terms "separation information" and "separation data" refer to data that indicates the presence or absence of chemical constituents with respect to the separation index. For example, separation data may indicate the presence of a chemical constituent having a particular mass eluting at a particular time. The separation data may indicate that the amount of the chemical constituent eluting over time rises, peaks, and then falls. A graph of the presence of the chemical constituent plotted over the separation index (e.g., time) may display a graphical peak. Thus, within the context of separation data, the terms "peak information" and "peak data" are synonymous with the terms "separation information" and "separation data".

As used herein, the term "Mass Spectrometry" (MS) refers to a technique for measuring and analyzing molecules that involves ionizing or ionizing and fragmenting a target molecule, then analyzing the ions, based on their mass/charge ratios, to produce a mass spectrum that serves as a "molecular fingerprint". Determining the mass/charge ratio of an object may be done through means of determining the wavelengths at which electromagnetic energy is absorbed by that object. There are several commonly used methods to determine the mass to charge ratio of an ion, some measuring the interaction of the ion trajectory with electromagnetic waves, others measuring the time an ion takes to travel a given distance, or a combination of both. The data from these fragment mass measurements can be searched against databases to obtain identifications of target molecules. Mass spectrometry is also widely used in other areas of chemistry, like petrochemistry or pharmaceutical quality control, among many others.

As used herein, the term "mass analyzer" refers to a device in a mass spectrometer that separates a mixture of ions by their mass-to-charge ratios.

As used herein, the term "source" refers to a device in a mass spectrometer that ionizes a sample to be analyzed.

As used herein, the term "detector" refers to a device in a mass spectrometer that detects ions.

As used herein, the term "ion" refers to any object containing a charge, which can be formed for example by adding electrons to or removing electrons from the object.

As used herein, the term "mass spectrum" refers to a plot of data produced by a mass spectrometer, typically containing m/z values on x-axis and intensity values on y-axis.

As used herein, the term "m/z" refers to the dimensionless quantity formed by dividing the mass number of an ion by its charge number. It has long been called the "mass-to-charge" ratio.

As used herein, the term "scan" refers to a mass spectrum that is associated with a particular separation index. For example, systems that use a chromatographic separation technique may generate multiple scans, each scan at a different retention time.

As used herein, the term "sample" is used in its broadest sense, and may include a specimen or culture, of natural or synthetic origin.

As used herein, the term "biological sample" refers to plant, fungus, or animal, including human, fluid, solid (e.g., stool) or tissue, as well as cell cultures and culture and fermentation media, liquid and solid food and feed products and ingredients such as dairy items, grains, vegetables, meat and meat by-products, and waste. Biological samples may be obtained from all of the various families of domestic animals, as well as feral or wild animals, including, but not limited to, such animals as ungulates, bear, fish, lagamorphs, rodents, etc. A biological sample may contain any biological material, and may comprise cellular and/or non-cellular material from a subject. The sample can be isolated from any suitable biological tissue or fluid such as, for example, prostate tissue, blood, blood plasma, urine, or cerebral spinal fluid (CSF).

As used herein, the term "environmental sample" refers to environmental material such as surface matter, soil, water and industrial samples, as well as samples obtained from food and dairy processing instruments, apparatus, equipment, utensils, disposable and non-disposable items. These examples are not to be construed as limiting the sample types applicable to the subject matter described herein.

Systems that couple the output of a liquid or gas chromatograph to the input of a mass spectrometer, such that the chromatograph separates the sample into chemical constituents, which are fed into the ion source of the mass spectrometer, exist. Conventional systems analyze the resulting mass spectrum by performing a best fit analysis of the mass spectrum recorded against libraries of mass spectrum data. However, this approach suffers several deficiencies.

First, compound library matching usually does not consider separation data, such as retention time or retention index. As a result, the system typically must attempt to identify a compound observed in the mass spectrum by comparing it to every compound in the library, regardless of the possibility that the library chemical entity would or would not have had the same separation characteristics as the compound being analyzed. In some cases, two different chemical constituents have the same mass, and are thus indistinguishable without chromatography data. The problem is further compounded when the separation technique used does not adequately separate the two chemical constituents having the same mass. In this situation, even if the system did consider separation data, the two constituents would appear together as a single peak rather than two peaks, and are again indistinguishable from each other.

Second, the libraries of mass spectrum data may be synthetic. As used herein, the term "synthetic library" refers to a library that was generated on another system or was generated in silico, i.e., based on hypothetical or calculated results, rather than on empirical results. Because synthetic libraries do not reflect the particular characteristics of the method and instrument that is used to actually perform the analysis, synthetic libraries may introduce error.

Third, conventional systems that have high accuracy, such as high accuracy mass spectrometers, commonly referred to as "accurate mass" systems, are expensive, and many have a lower duty cycle than their standard counterparts. Thus, in conventional systems, there may be a tradeoff between accuracy and throughput. Furthermore, accurate mass alone is insufficient for high confidence identification of a chemical constituent. For example, the amino acids leucine and isoleucine have identical mass, because they have the same combination of atoms, but arranged in slightly different locations on the respective molecule. Accurate mass alone cannot differentiate between them. Accurate mass is neither a prerequisite nor a guarantee of accurate identification of chemical constituents.

Fourth, some conventional systems perform "targeted" analysis, meaning that they are configured to look for and identify specific chemical constituents. Such systems cannot perform "non-targeted" analysis, which attempts to detect and identify all chemical constituents of a sample, including hitherto unknown entities. Non-targeted analysis is an approach that has enormous potential application and benefits. For example, metabolomic analysis, which analyzes the metabolites or by-products of cellular processes, is useful to monitor in a non targeted manner (i.e., globally), changes in metabolic profiles related to age, gender, or other factors (e.g., health or disease status), and can be extended to detect dietary metabolites as well as drugs, medications, and other xenobiotics (chemical substances that are found in an organism but which are not normally produced or expected to be present in the organism) that are present in the sample matrix. The ability to determine the composition of chemical constituents in a complex mixture in a non-targeted manner can be useful in a variety of other contexts. One such context is bioprocessing, which is the growth of cells to produce drugs, enzymes, chemicals, additives, and other useful products. Other contexts include analysis of biological and environmental samples.

Accordingly, there exists a need to provide systems and methods for more accurately determining, in a non-targeted manner, the composition of chemical constituents in a complex mixture.

SUMMARY

According to one aspect, a method for non-targeted determination of composition of chemical constituents in a complex mixture includes generating, using a separation technique and a mass spectrometer, separation and mass spectrometry data of a sample, where the separation data includes peak information and where the mass spectrometry data includes primary and secondary mass spectrometry data. The analysis results, including the generated separation and mass spectrometry data, are collected and stored. A chemical constituent of the sample is determined by comparing the analysis results to a library of information indicating characteristics of chemical entities, the characteristics including separation and mass spectrometry data. The comparison is based on the separation and mass spectrometry data. The library of information includes data generated by the separation technique and mass spectrometer, and also includes separation and mass spectrometry data for both identified and unidentified chemical entities. An indication of the chemical constituent of the sample is made available in human-accessible form.

As used herein, the term "identified chemical entities" refers to chemical entities which have been identified to a high degree of confidence, while the term "unidentified chemical entities" refers to chemical entities that have been detected as a chemical constituent in a complex mixture, but which have not been so identified.

As used herein, the term "recognition" as applied to unidentified chemical entities refers to the determination that the unidentified chemical entity is a constituent in a complex mixture based on a comparison of the analysis results to the characteristics of the unidentified chemical entity recorded in the library of information. Recognition is not synonymous with identification. An example of recognition is the determination of the presence of a chemical constituent having a particular retention index and mass-to-charge ratio, whose presence had previously been detected and for whom an entry had been added to the library of information, the entry including chromatography and mass spectrometry data associated with the entity.

As used herein, the term "identification" as applied to chemical entities refers to the high confidence determination of the identity of a chemical entity. An example of identification is the determination that a molecule having 7 carbon atoms, 7 hydrogen atoms, a nitrogen atom, and 2 oxygen atoms is anthranilic acid rather than salicylamide, both of which have same chemical formula $C_7H_7NO_2$.

As used herein, the term "making available in human-accessible form" includes presenting information to a user visually, aurally, or by touch (e.g., using Braille), and includes displaying information on a screen, creating printed material including the information, and storing the information in a form that can be accessed using a computer application, such as a word processor, spreadsheet program, a text editor, etc.

According to another aspect, a system for non-targeted determination of composition of chemical constituents in a complex mixture includes a separation tool for separating chemical constituents of a sample and generating separation data, a mass spectrometer for performing mass spectrometry on portions of the separated chemical constituents of the sample and generating mass spectrometry data, where the separation data includes peak information and the mass spectrometry data includes primary and secondary mass spectrometry data. The system includes a library of information indicating characteristics of chemical entities, the characteristics including separation and mass spectrometry data. The library of information includes data generated by the separation tool and mass spectrometer and includes separation and mass spectrometry data for identified and unidentified chemical entities. The system also includes an analysis module for receiving and collecting and storing as analysis results the separation and the mass spectrometry data. A chemical constituent of the sample is determined by comparison of the analysis results to the library of information, where the mass spectrometry data includes primary and secondary mass spectrometry data and where the comparison is based on the separation and mass spectrometry data. The system includes user interface, coupled to the analysis module, for making available in human-accessible form an indication of the chemical constituent of the sample.

The subject matter described herein for non-targeted determination of the composition of chemical constituents in a complex mixture may be implemented in hardware, software, firmware, or any combination thereof. As such, the terms "function" or "module" as used herein refer to hardware, software, and/or firmware for implementing the feature being described. In one exemplary implementation, the subject matter described herein may be implemented using a computer program product comprising computer executable instructions embodied in a computer readable medium.

Exemplary computer readable media suitable for implementing the subject matter described herein include disk memory devices, chip memory devices, programmable logic devices, and application specific integrated circuits. In addition, a computer program product that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings, wherein like reference numerals represent like parts, of which:

FIG. 1B illustrates analysis results collected by an exemplary system according to an embodiment of the subject matter described herein;

FIG. 1C is an illustration of example scan data according to an embodiment of the subject matter described herein;

FIGS. 2A through 2D illustrate exemplary data structures for storing chromatography and mass spectrometry results information according to an embodiment of the subject matter described herein;

FIGS. 2E and 2F illustrate exemplary data structures for storing information about chemical entities according to embodiments of the subject matter described herein;

FIGS. 4A through 4H, 4J through 4N, 4P through 4W, and 5A through 5E represent information displayed to a user of a system according to an embodiment of the subject matter described herein.

DETAILED DESCRIPTION

In accordance with the subject matter disclosed herein, systems, methods, and computer readable medium are provided for determining composition of chemical constituents in a complex mixture.

Figure 1A:
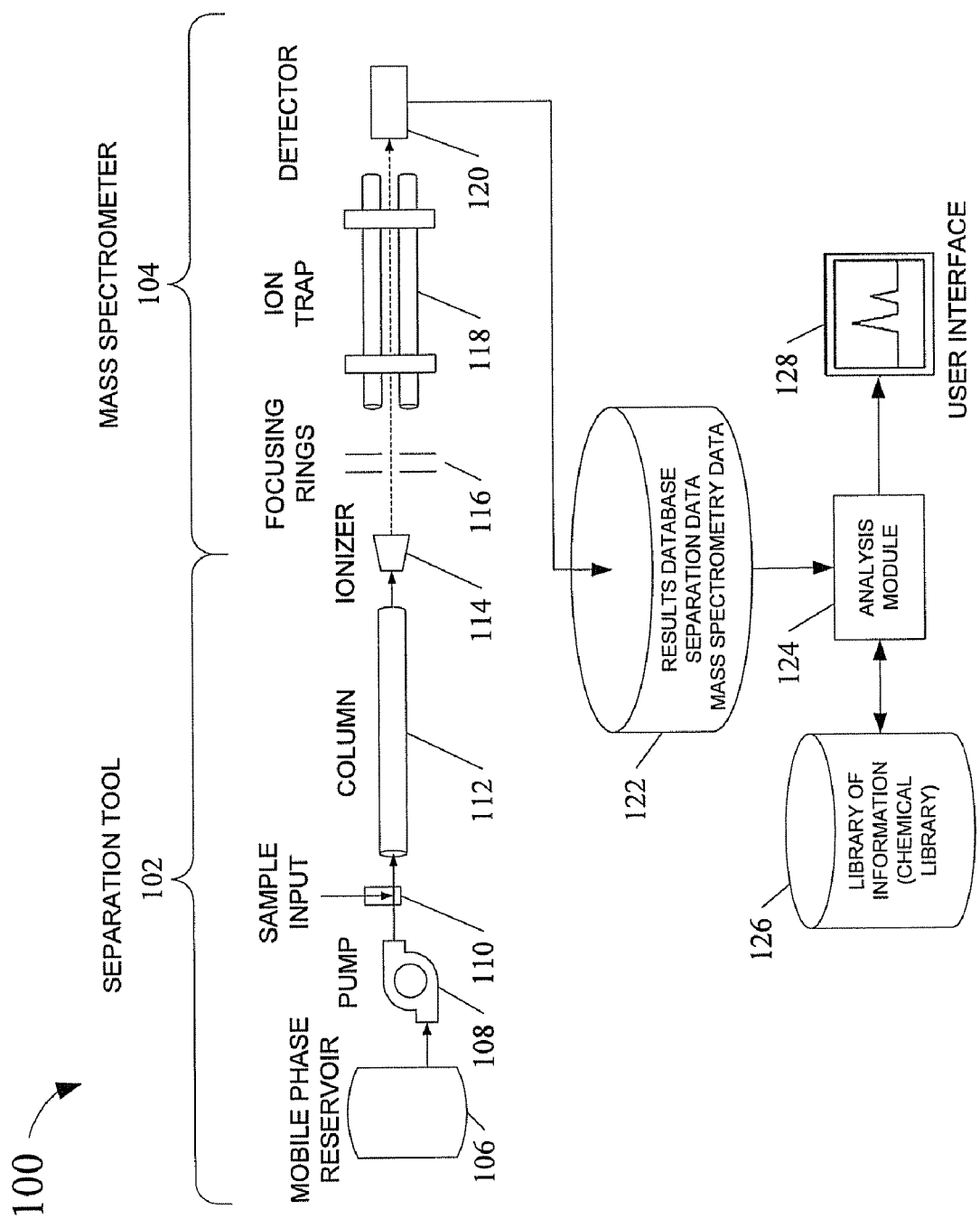
FIG. 1A is a block diagram illustrating an exemplary system for determining composition of chemical constituents in a complex mixture according to an embodiment of the subject matter described herein.

FIG. 1A is a block diagram illustrating an exemplary system for determining composition of chemical constituents in a complex mixture according to an embodiment of the subject matter described herein. System 100 includes a component for performing a separation technique for separating a sample to be analyzed into chemical constituents. In one embodiment, system 100 includes a chromatograph 102 section for performing the separation and a mass spectrometer (MS) 104 for performing mass spectrometry on the effluent of (i.e., the chemical constituents that elute from) chromatograph 102. In one embodiment, chromatograph 102 is an ultra-high pressure liquid chromatograph (UHPLC). Alternatively, other chemical separation methods could be used that are amendable to the analysis of small molecules, i.e., with a molecular mass of less than 2,000 daltons, that result in a parameter that is characteristic of a given chemical species, and are compatible with any atmospheric pressure or soft desorption ionization technique. Other separation methods include ion-mobility spectrometry (IMS), capillary zone electrophoresis (CZE), high-performance liquid chromatography (HPLC), and monolithic liquid chromatography.

In the embodiment illustrated in FIG. 1, system 100 includes a mobile phase reservoir 106 and a pump 108 for forcing the mobile phase and a sample, injected into the mobile phase via sample input 110, through column 112 at high pressure. Various chemical constituents of the sample will elute through column 112 at different speeds and thus exit column 112 at different times. The time that a chemical constituent of the sample takes to travel through and exit column 112 is referred to as the retention time of the chemical constituent.

The output of column 112 is fed into an ionizer 114. For systems using liquid chromatographs, ionizer 114 may also convert the effluent exiting from column 112 into an ionized gas. For example, ionizer 114 may be an electro-spray ionization device (ESI), an atmospheric pressure chemical ionizer (APCI), or other atmospheric pressure or soft desorption ionization technique. The ionized gas passes through focusing rings 116 and into the mass analysis section of MS 104. In the embodiment illustrated in FIG. 1, the mass analysis section of MS 104 is a quadrupole ion trap 118 coupled to a detector 120. Alternative embodiments may employ a time-of-flight mass spectrometer, a quadrupole mass spectrometer without an ion trap, and mass spectrometers with other types of ion traps.

Detector 120 data is collected and stored in a results database 122 for storing separation and mass spectrometry data. Alternatively, the separation and mass spectrometry data may be stored in tables or other data structures, in memory or on storage devices, or via other data storage means known in the art. In the embodiment illustrated in FIG. 1, results database 122 may be used for storing chromatography and mass spectrometry data. For example, results database 112 may include liquid chromatography and mass spectrometry (LC/MS) data. In alternative embodiments, other types of separation data may be stored in results database 112.

System 100 also includes an analysis module 124 for determining the composition of the sample based on a comparison of the analysis results to a library of information listing characteristics of various chemical entities, chemical library 126. System 100 may include a user interface UI 128, such as a graphical user interface (GUI). A user may use UI 128 to, for example, direct the system to perform the separation and mass spectrometry steps, view the results, direct the system to perform additional separation or mass spectrometry steps, and instruct the system to perform automated comparison and identification routines to determine the composition of the sample based on best matches with entities in the chemical library 126. The user may also use UI 128 to access the chemical library 126, manually compare library entities with analysis results, or review/confirm the conclusions of the automated identification routines.

FIG. 1B illustrates a plot of analysis results that may be collected by an exemplary system according to an embodiment of the subject matter described herein. The three dimensional plot shown in FIG. 1B displays retention time or retention index on the X axis, m/z on the Y axis, and intensity on the Z axis. In one embodiment, as chemical constituents exit column 112, mass spectrometer 104 generates a series of mass spectrums, or scans, at different retention times. The width along the X-axis of example scan 130 shown in FIG. 1B is exaggerated for visibility. Each scan 130 may show graphical peaks in the mass axes, commonly referred to as "ions", even though it is possible that a single graphical peak represents multiple chemical entities of the same m/z ratio and that eluted at the same time (i.e., the time that the scan was taken). In the example illustrated in FIG. 1B, scan 130 contains several peaks, including mass peak 132, representing an ion having a m/z ratio of 283.02 and a relative abundance of 100%. To the left of an immediately adjacent to peak 132 is another peak having a m/z ratio of 280.02 and a relative abundance of approximately 75%. Other ions having a much smaller relative abundance (<15%) are shown, having m/z ratios of 200.07, 362.92, 385.01, etc.

FIG. 1C illustrates example scan data. A scan may show peaks and valleys corresponding to the relative numbers of ions of a particular m/z ratio detected as illustrated in panel A of FIG. 1C. Mass peaks illustrated in panel A of FIG. 1C may also be represented in 'stick' form as illustrated in panel B of FIG. 1C. The stick representation is called centroid mass peak data and the size of the data file is reduced. For embodiments that use other separation techniques, such as techniques that physically separate the chemical constituents electrophoretically, for example, each scan may be associated with a distance or a normalized distance, rather than a retention time or a normalized retention time (e.g., a retention index).

When multiple scans are arranged along the axis representing separation (e.g., according to time for chromatographic separation techniques, or according to position for physical separation techniques), the intensity values for each ion can be observed to rise and fall, generating a chromatographic peak along the X axis, each chromatographic peak being associated with a particular m/z ratio. For simplicity, the term "chromatographic peak" will be used to refer generically to a peak representing the presence or absence of one or more ions across the axis representing separation (e.g., time, distance, etc.) In FIG. 1B, the two dimensional plot 134 shows chromatography data for the injection, where the peaks represent the changing presence of ions of a particular m/z over time. In the example illustrated in FIG. 1B, chromatographic plot 134 shows ions having a m/z ratio in the range 200.00–200.25, and peak 136 represents the presence of an ion having a m/z ratio of 200.06 and eluting from approximately 3.0 minutes until approximately 3.1 minutes, with a peak maximum at 3.02 minutes.

The separation and mass spectrometry data are hereinafter collectively referred to as "analysis results". Analysis results may include data from one or more analysis runs of a sample, data from different kinds of analysis on a sample, and data from analysis of different samples. Analysis results stored in results database 122 include separation and mass spectrometry information. Separation information may include peak information. For systems that use a chromatography technique for separation, separation information may include retention information, such as retention time and/or retention index of a peak. Peak information may include information describing the peak, including: intensity of a peak; width of the base of a peak; retention time of the start and end of the base of a peak; intensity of the start and end of the base of a peak; width of a peak at half of the peak's height; area of a peak; a symmetry of a peak; noise of a peak; a mass associated with a peak; a mass-to-charge ratio associated with a peak; an association of a peak to an entity in an ion tree describing parent-child relationships between ions; and a list of scans associated with a peak.

Analysis results may include data produced by tandem MS. As used herein, the term "tandem MS" refers to an operation in which a first MS step, called the "primary MS", is performed, followed by performance of one or more of a subsequent MS step, generically referred to as "secondary MS". In the primary MS, an ion, representing one (and possibly more than one) chemical constituent, is detected and recorded during the creation of the primary mass spectrum. The substance represented by the ion is subjected to a secondary MS, in which the substance of interest undergoes fragmentation in order to cause the substance to break into sub-components, which are detected and recorded as a secondary mass spectrum. In a true tandem MS, there is an unambiguous relationship between the ion of interest in the primary MS and the resulting peaks created during the secondary MS. The ion of interest in the primary MS corresponds to a "parent" or precursor ion, while the ions created during the secondary MS correspond to sub-components of the parent ion and are herein referred to as "child" or "product" ions.

Thus, tandem MS allows the creation of data structures that represent the parent-child relationship of chemical constituents in a complex mixture. This relationship may be represented by a tree-like structure illustrating the relationship of the parent and child ions to each other, where the child ions represent sub-components of the parent ion. Tandem MS may be repeated on child ions to determine "grand-child" ions, for example. Thus, tandem MS is not limited to two-levels of fragmentation, but is used generically to refer to multi-level MS, also referred to as "$MS^n$". The term "MS/MS" is a synonym for "$MS^2$". For simplicity, the term "child ion" hereinafter refers to any ion created by a secondary or higher-order (i.e., not the primary) MS.

For example, a primary mass spectrum might contain five distinct ions, which may be represented as five graphical peaks; each ion in the primary MS may be a parent ion. Each parent ion may be subjected to a secondary MS that produces a mass spectrum showing the child ions for that particular parent ion. In one embodiment, an intensity threshold value may be set for the primary MS, such that detection of an ion having an intensity higher than the intensity threshold value automatically triggers the performance of a secondary MS. In this example, a substance may undergo separation by the chromatography step, separating into chemical constituents X, Y, and Z, each of which elutes at a different time. Chemical constituent X enters the source of the mass spectrometer and is ionized (and possibly fragmented) into several ion species, for example $X1$, $X2$, and $X3$, which are recorded as several ions in the primary mass spectrum. One of the ions in the primary mass spectrum, e.g., $X2$, may be above the intensity threshold value, triggering performance of a secondary MS.

In one embodiment, during the time that constituent X is undergoing the primary MS, constituent X may continue to elute from the chromatograph, but be disregarded by the mass spectrometer. If, at the time that the secondary MS is triggered, constituent X is still being eluted, another sample may be accepted by the MS source, and secondary MS may be performed on the second sample of constituent X. This second sample may be ionized (and possibly fragmented) into $X1$, $X2$, and $X3$ as before, but where $X2$ is trapped by an ion trap while $X1$ and $X3$ are expelled from the ion trap. $X2$ may then be fragmented, for example into sub-components $X2A$ and $X2B$. If constituent X is still being eluted from the chromatograph, additional secondary MS may be performed, e.g., determining sub-components of $X3$, or even higher order MS may be performed. For example, tertiary MS may be performed on $X2A$ to determine its component parts, $X2Ai$, $X2Aii$, and so on.

This example illustrates the point that by using tandem MS, the parent ion, $X2$, is unambiguously related to its child ions, $X2A$ and $X2B$, and that relationship includes information about the relative mass-to-charge ratios of the parent and child ions.

Unambiguously understanding the relationship of both mass-to-charge and relative intensities of the child ions and the parent ion enables a powerful technique herein referred to as "ion accounting" in which all of the ions generated in an analysis run are surveyed and an attempt is made to assign them all to a chemical entity. Any ions that cannot be assigned to a chemical entity may be novel chemical constituents in the mixture; in this case, a new library entry can be made for these ions, as appropriate. Thus, hitherto unknown chemical constituents may be detected, and information describing their attributes may be stored in order that the presence of the unknown chemical constituent may be subsequently detected, i.e., recognized, even though the identity of the constituent is unknown. In this manner, new or unknown chemical constituents may be detected, subsequently recognized, and eventually identified.

The parent/child relationship may be extended also to describe the relationship between separated components (e.g., components eluting from the chromatography stage) and ions detected in the primary MS, and even to the relationship between the sample to be analyzed and the separated components.

In addition, analysis results in results database 122 may include information describing the general nature of the analysis results or other meta-data. Examples include: the number of primary scans taken during an analysis; the number of secondary scans taken during an analysis; the percentage of secondary scans actually taken versus secondary scans that could have been taken; the number of secondary scans taken that were within the peak of an identified chemical entity; the percentage of secondary scans taken that were with the peak of an identified chemical entity; the number of peaks recorded during an analysis; the number of peaks for which a secondary scan has been taken; the percentage of peaks for which a secondary scan has been taken; the number of peaks that have more than one secondary scan associated with it; the percentage of peaks that have more than one secondary scan associated with it; the area of the largest peak for which a secondary scan was not performed; and the area of the smallest peak for which a secondary scan was performed.

Analysis module 124 may determine the chemical constituents of the sample based on a comparison of one or more characteristics of the sample to information about chemical entities stored in chemical library 126. In one embodiment, the comparison is based on both retention information and peak information. Information stored in chemical library 126 may include retention time, retention index, masses seen in primary scans, including adducts, isotope relationships, in-source fragmentation, and relative intensities of the above. Library entries may be organized into a tree structure with fragment, sub-fragment, and sub-sub-fragment data, e.g., parent-child ion data generated by $MS^n$, traceable to any ion, and where ions can be identified as chemical constituents of molecules, including adducts or isotopes. Library entries may also include structural information, physical properties, list of physical stocks, links to public chemical database, links to various library entries, and links to actual instrument data run on stock chemicals. The term "authenticated library entry" refers to a library entry that contains information about a chemical entity of undisputed identity that has been analyzed using the actual instrument.

In one embodiment, chemical library 126 may be used to store information about an unknown or unidentified chemical constituent within a sample. Information about the unknown ion, such as its retention time, mass to charge ratio, and other information, may be stored for subsequent comparison during analysis of another sample. In this manner, hitherto unknown ions may be detected and subsequently identified over a series of analysis runs. Unlike conventional chemical assays, which test a sample against a finite number of known chemical constituents, the subject matter described herein can be used to detect and ultimately identify any and all chemical constituents, even previously unknown chemical entities, of a complex mixture.

Analysis module 124 is configured to determine the composition of the sample based a comparison of one or more sets of information from three sources of information: 1) separation data, such as retention window (retention time, retention index); 2) mass of molecular ion in the primary MS scan; and 3) fragmentation pattern of secondary MS scan (i.e., MS/MS or MS").

In one embodiment, the analysis results and information about chemical entities may be stored in relational database structure. FIGS. 2A through 2D illustrate exemplary data structures for storing results information in results database 122, and FIGS. 2E and 2F illustrate exemplary data structures for storing information about chemical entities in chemical library 126 according to embodiments of the subject matter described herein.

FIG. 2A illustrates an exemplary table structure for storing results of a particular scan. Each entry in table "MBZR_SCANS" includes information such as retention time, scan number, mass, and the intensity data array.

FIG. 2B illustrates an exemplary table structure for modeling the mass spectrometry tree structure with links to the scan data. Each entry in table "CHRO_ION_TREES" includes information such as the identity of a parent node, the mass of a linking ion, retention information, and a reference to scan data.

FIG. 2C illustrates an exemplary table structure for storing peak information. Peaks table "MBZR_PEAK" may contain chromatographic peaks characterized by mass, retention time or retention index, area under the peak, and other lesser peak characteristics such as noise. For example, a single analysis may produce a set of mass spectrums having a certain number, P, of detectable peaks, in which case P entries may be added to the peaks table, one entry per detected peak.

FIG. 2D illustrates an exemplary table structure for organizing sets of chromatographically related peaks. Each entry in table "MBZR_COMPONENT" may associate a chemical constituent to peaks detected at a particular retention time in one or more scans.

FIGS. 2E and 2F illustrate exemplary table structures for entries in chemical library 126 according to an embodiment of the subject matter described herein. In one embodiment, molecule information, such as name, structure, compounds, melting points, etc., may be stored separately from chemical entity information, such as RT/RI, the type of run (e.g., LC+/−, MS+/−, MS"), masses (e.g., M+H, 2M+H, ion fragments, adducts), and pointers to fragment information. A chemical entity, if identified, can point back to the reference molecule.

Figure 3:
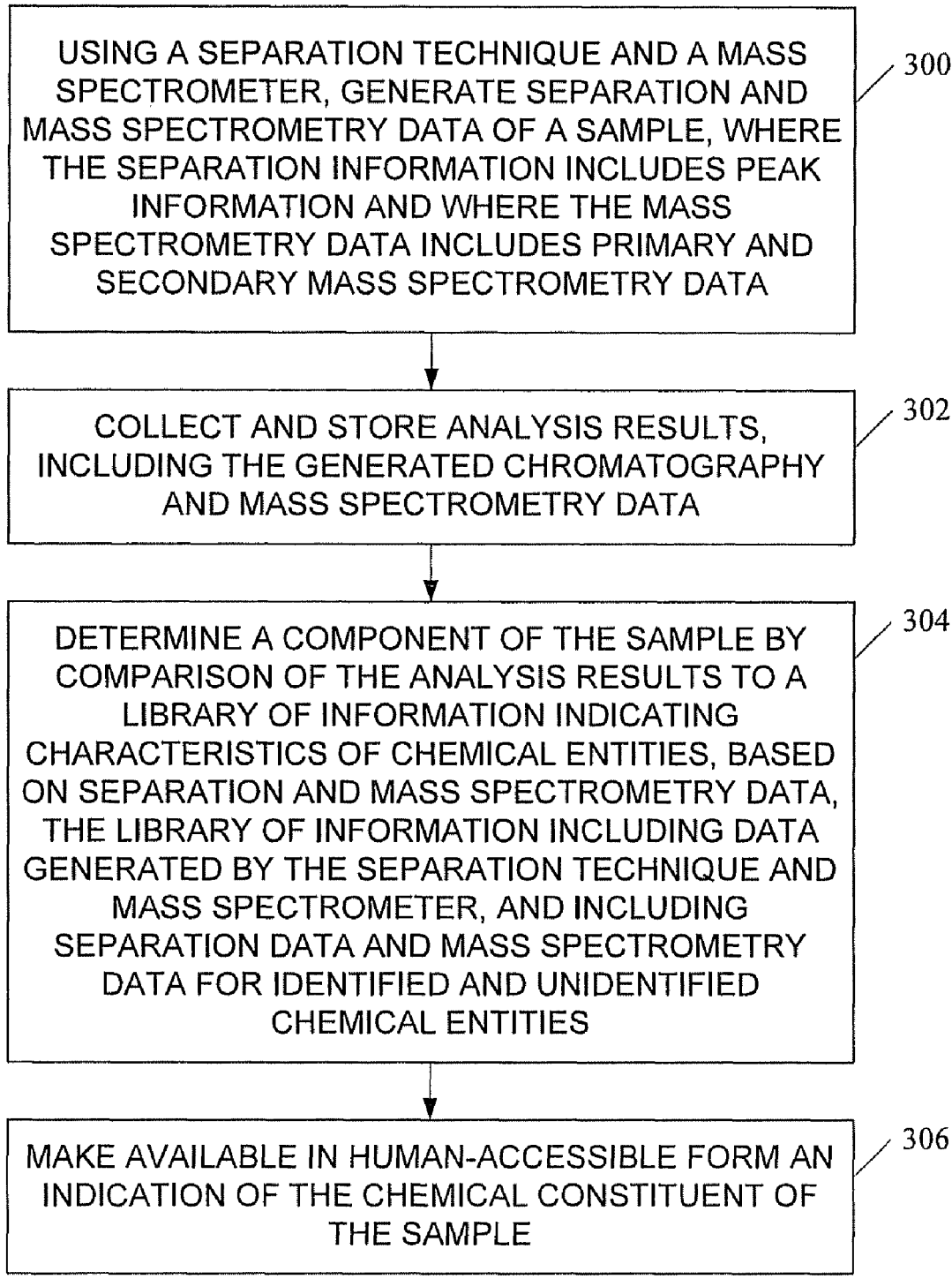
FIG. 3 is a flow chart illustrating an exemplary process for determining composition of chemical constituents in a complex mixture according to an embodiment of the subject matter described herein.

FIG. 3 is a flow chart illustrating an exemplary process for determining composition of chemical constituents in a complex mixture according to an embodiment of the subject matter described herein.

At block 300, chromatography and mass spectrometry data of a sample is generated using a chromatograph and a mass spectrometer. The generated data includes peak information and retention information. In the embodiment illustrated in FIG. 1, a sample injected into sample input port 110 will elute through column 112. If chromatograph 102 is a form of liquid chromatograph, such as UHPLC, ionizer 114 may be an electrospray ionization (ESI) device, which simultaneously ionizes the effluent and converts the effluent from liquid phase to gas phase. The ionized particles thus enter the mass spectrometer 104. In one embodiment, the ionized particles pass through focusing rings 116 and into the mass analyzer section of mass spectrometer 104, such as through quadrupole ion trap 118 and into detector 120.

At block 302, the generated chromatography and mass spectrometry data is collected and stored. For example, peak information, such as intensity, along with retention information, such as retention time and retention index, may be recorded into results database 122.

Multiple chromatography and/or mass spectrometry runs may be performed on a sample, and the data collected and stored for analysis. For example, a sample may be subjected to both an acidic and a basic liquid chromatography, i.e., a liquid chromatography that uses a mobile phase that encourages creation of positive or negative ions, respectively. A sample may be subjected to both a positive ion and a negative ion mass spectrometry. Multiple runs may be performed on the same sample. All of the data described above may be stored in results database 122.

In one embodiment, system 100 is configured to perform tandem MS. As used herein, the term "tandem MS" refers to any technique where a parent molecule, ion, or chemical entity for which mass spectrometry data is known is further fragmented and mass spectrometry information is collected for the fragments. This encompasses any technique whereby all fragments from a given molecule are ascribed to that molecule via some process that occurs based on the inner workings of the device. As used herein, the terms "tandem MS" and "multi-stage MS" are synonymous. For example, system 100 may perform true tandem MS by means of an ion trap, or it may perform an equivalent to true tandem MS by using a triple quadrupole MS, or by any technique that allows isolation and further fragmentation of an individual mass.

It can be readily appreciated that mass spectrometry (or tandem MS) may be performed on each and every separate chemical constituent that elutes from column 112, but also that mass spectrometry may be performed on only a subset of the chemical constituents of the sample as they emerge from column 112, according to the goals of the analysis as defined by the user and performed by system 100.

At block 304, a chemical constituent of the sample is determined by comparing the analysis results to a library of information indicating characteristics of chemical entities, such as chemical library 126. In one embodiment, analysis module 124 may make a best guess as to the identity of the chemical entity represented by a peak, based on matching of the characteristics listed above. In this manner, a peak may be associated with an entity listed in chemical library 126. In one embodiment, the entity associated with the peak may be a node on an ion tree which describes parent child relationships between ions. In one embodiment, the peak may be associated with a list of scans whose data displayed the peak.

At block 306, an indication of a chemical constituent of the sample is make available in human-accessible form. In one embodiment, user interface 128 may provide a visual indication of the chemical constituent. For example, UI 128 may display analysis results showing chemical constituents that have been detected or identified. Alternatively, user interface 128 may generate graphic, text, or Braille printouts; may generate audio, such as computer-generated speech; or may generate emails, text messages, or computer files, such as text documents, spreadsheets, databases, etc.

The systems and methods described above have several advantages over conventional systems and methods. First, unlike conventional chromatography+mass spectrometry systems, which try to identify the chemical constituents represented by a peak using only the peak data, analysis module 124 performs a comparison based on both peak information and retention information. By considering retention time/retention index of a peak, analysis module 124 can significantly reduce its search space, eliminating molecules that are known to have retention information other than the retention information measured for the peak in question. Furthermore, because a molecule may have one retention time for a LC+ run and a different retention time for a LC− run, if a sample shows peaks in the expected places for different types of LC runs, there is a higher confidence that the sample contains the molecule in question.

Similarly, because analysis module 124 may consider not only multiple analysis runs of different types, but also perform tandem or multi-stage mass spectrometry, the wealth of data produced by the analysis runs may be matched not only for parent molecules, but for child molecules or ions, or other fragments, as well. This also gives rise to higher confidence that the chemical constituent within the sample has been correctly identified.

Second, the library of information 126 contains authentic data, i.e., data that was generated by the separation tool and mass spectrometer using a reference standard. Unlike synthetic data, which is data generated in silico, e.g., based on hypothetical or modeled behavior, authentic data is based on results recorded using the same method of analysis on the same equipment being used to analyze the sample. Thus, for a particular molecule, the library information for that molecule will more closely match analysis results for a sample containing that molecule. This is particularly important for labs or shops that have fine tuned their system, such as using a custom mobile phase composition for positive LC and another custom mobile phase composition for negative LC, for example.

Third, the library of information may include chromatography and mass spectrometry data for unidentified chemical entities as well as for identified chemical entities. Although in the embodiment illustrated in FIG. 1, results data 122 is shown as separate from chemical library 126, alternative embodiments may use single database, table, etc., for storing results data and library data together. Even if the results data is conceptually separate from library data, as shown in FIG. 1, analysis module 124 may be configured to detect that an unknown, as yet unidentified peak keeps showing up in the results database 122, and create an entry for the mystery molecule in chemical library 126. In this manner, system 100 is able to report the presence or absence of this mystery molecule even though the identity of the molecule is unknown. System 100 may report ion alignment over a sample set, and may identify and categorize ions. For example, analysis module 124 may match ions versus a library at $MS^n$ level on all ions, and flag for subsequent review by a user or for subsequent processing by system 100 any ions that are unaccounted for.

This ability to perform non-targeted analysis, such as initial detection and subsequent recognition of unknown metabolites, has enormous benefits. For example, in a metabolic analysis of cells with and without cancer, if the analysis results show that cancerous cells almost always contain some mystery molecule while healthy cells do not, this gives important direction to research for detection or treatment of that cancer.

In one embodiment, determining the composition of the sample may include displaying library information for a particular entity along with analysis results so that a user may perform a visual comparison of the two, or visually confirm the correctness of the comparison performed by the system. UI 128 may allow a user to perform a first analysis of a sample, and view the results of the first analysis.

FIGS. 4A-4H, 4J through 4N, 4P through 4W, and 5A through 5E represent information displayed to a user via UI 128, according to an embodiment of the subject matter described herein. In the embodiments illustrated in FIGS. 4A-4H, 4J through 4N, 4P through 4W, and 5A through 5E the separation technique is assumed to be some form of chromatography, and the separation information includes retention time and/or retention index. This is intended as an illustrative example embodiment, and is not a limitation of the subject matter described herein.

Figure 4A:
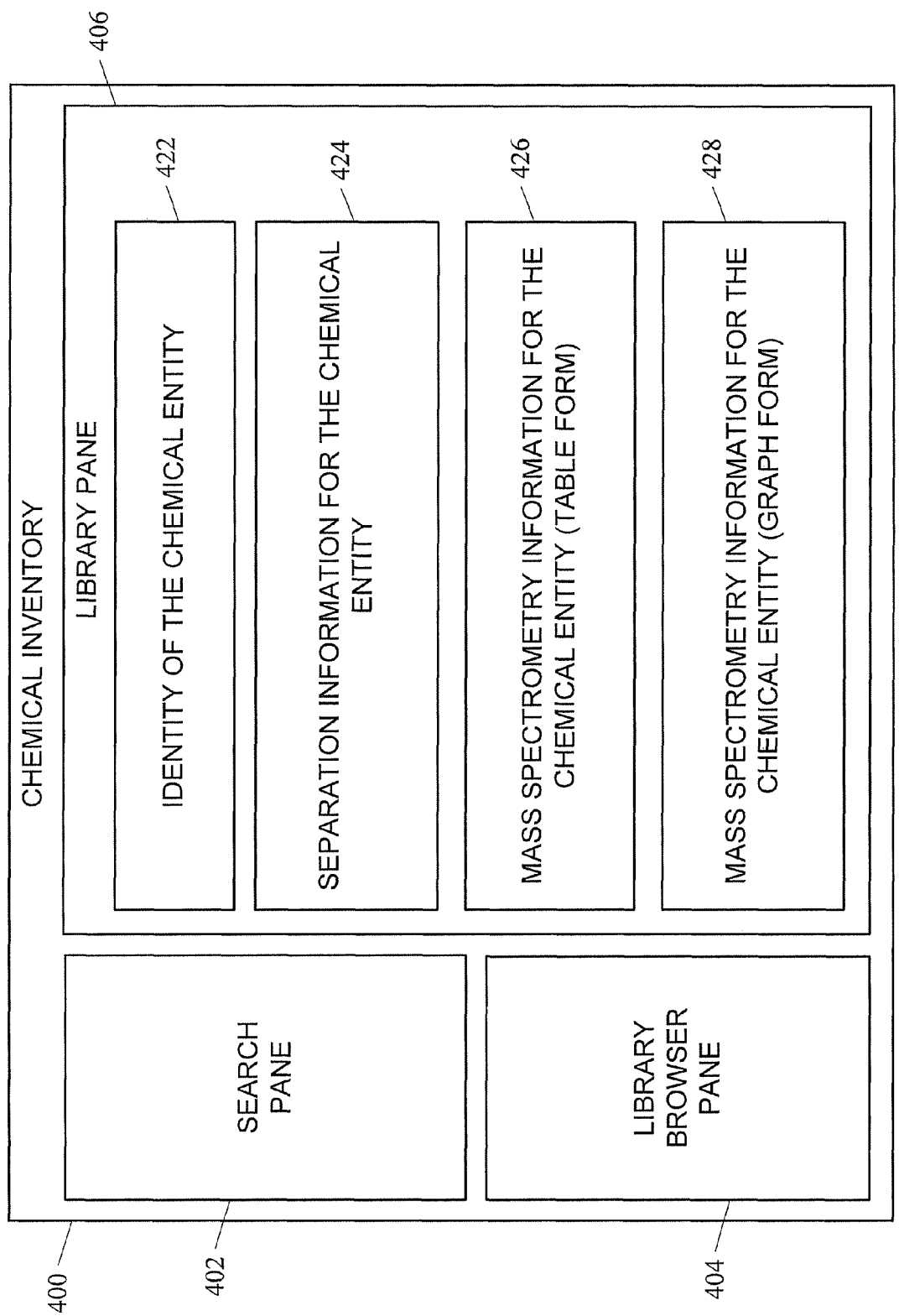

FIG. 4A represents information about a library entry in chemical library 126 as displayed to a user via UI 128. FIG. 4A shows a window 400 titled "Chemical Inventory", which includes a search pane 402 on the upper left, a library browser pane 404 on the lower left, and a library pane 406 on the right side of window 400.

Figure 4B:
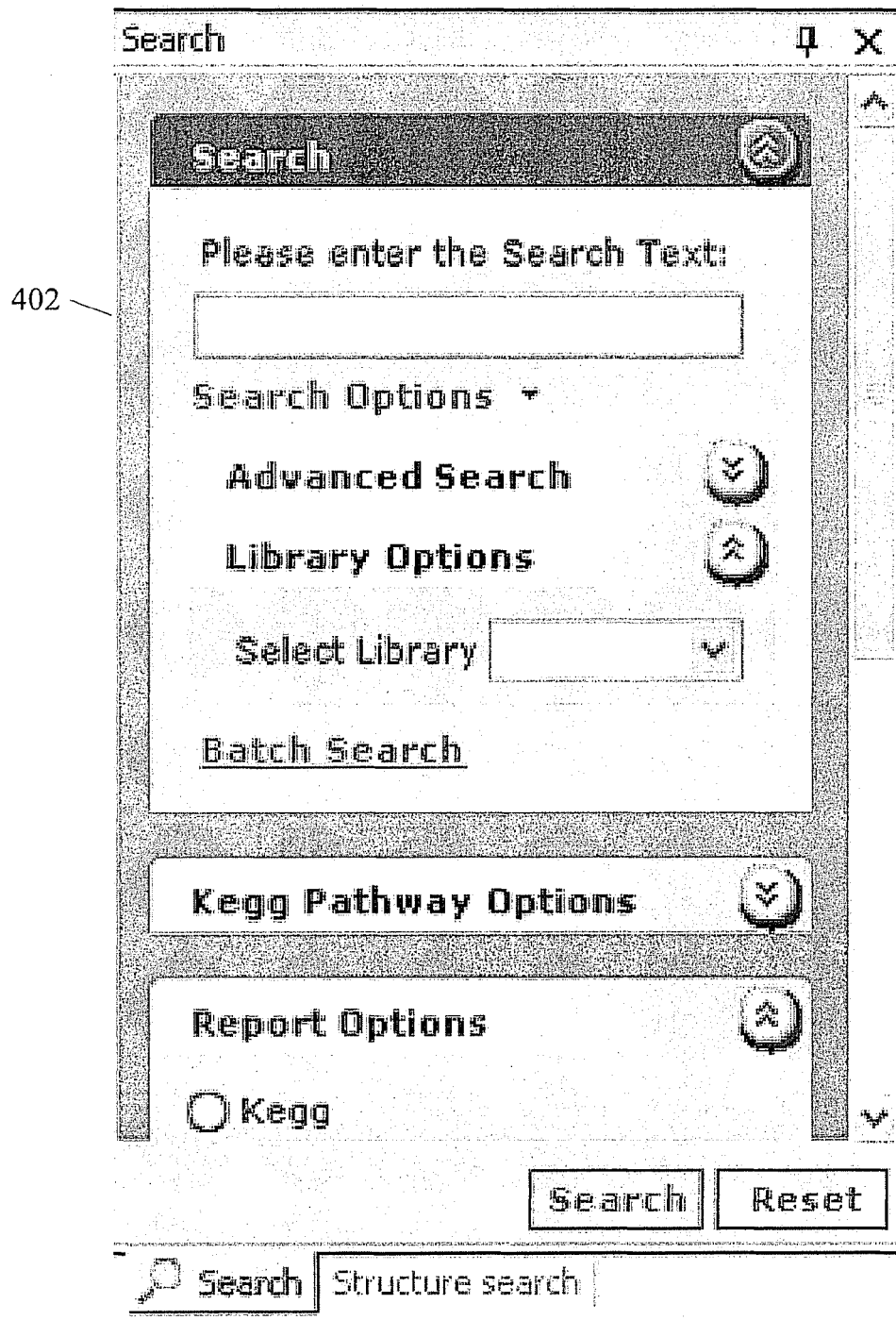
Figure 4C:
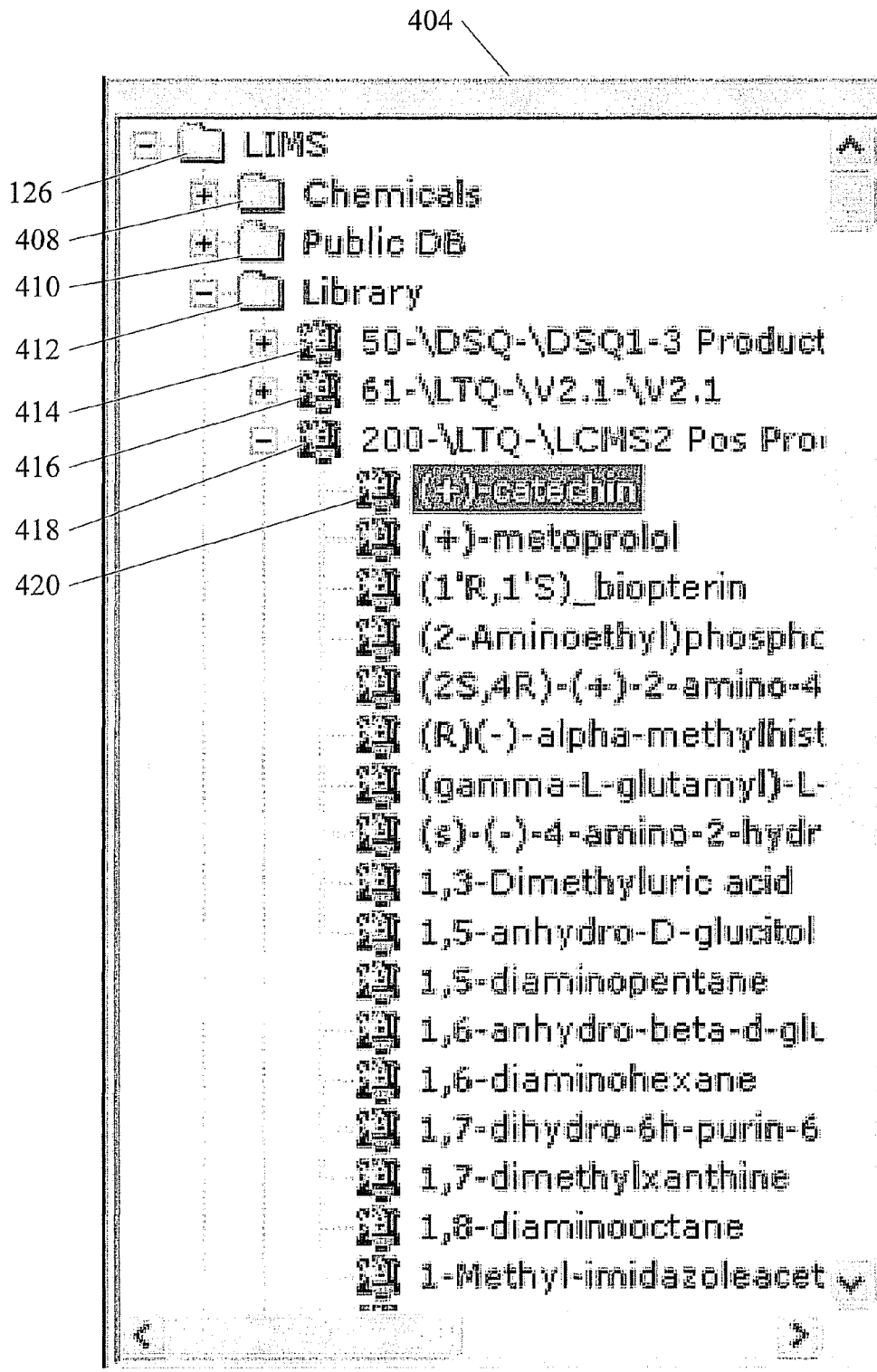

FIG. 4B is a screen shot showing search pane 402 in more detail. A user may use search pane 402 to search the various libraries of information. FIG. 4C is a screen shot showing library browser pane 404 in more detail. A user may use library browser pane 404 to browse various databases or libraries of information. In the embodiment illustrated in FIG. 4C, library browser pane 404 shows chemical library 126—named "LIMS" in this example—arranged in a hierarchical tree structure. Although the structure of chemical library 126 is displayed in library browser pane 404 as a hierarchy of folders (directories) containing sub-folders (sub-directories) and entities (files), the actual library structure is not limited to a file/directory implementation, but may be implemented as files, directories, a database, data stored in volatile or non-volatile memory, disk or memory storage devices, compact disks, or other means for storage and/or organization of data, in any combination. In the embodiment illustrated in FIG. 4C, chemical library (LIMS) 126 includes a library of information about individual chemicals (Chemicals) 408, links to public databases or data culled therefrom (Public DB) 410, and a library (Library) 412 of authenticated chemical entities and information on recognized but not yet identified chemical entities.

In one embodiment, Chemicals 408 may include information about each Individual chemical entity that does not vary depending on the separation or mass spectrometry technique used. Such information may include molecular structure, molecular formula, classification, and standard name or names. In contrast, Library 412 may include information about each individual chemical entity that does depend on the separation or mass spectrometry technique used, such as its retention time. For example, the same chemical entity may have completely different retention times depending on whether a gas or liquid chromatograph was used, whether the mobile phase used during the separation step was acidic or basic, and so on. In these embodiments, the equipment-specific data may be stored in Library 412 while the intrinsic characteristics of the chemical entity may be stored in Chemicals 408. In one embodiment, entries in Chemicals 408 and Library 412 may cross reference each other and both may cross-reference entries in Public DB 410 or other sub-components of LIMS 126.

In the embodiment illustrated in FIG. 4C, Library 412 is organized into multiple sub-libraries, 414, 416, and 418, each representing a type of analysis or combination of equipment. For example, sub-library 414 may contain authenticated results of chemical entities that have been separated using gas chromatography, while sub-library 416 may contain authenticated results of chemical entities that have been separated using ultra-high pressure liquid chromatography. Sub-library 418 may contain chromatography and mass spectrometry information that has been collected but not yet authenticated, and so on. Each sub-library may contain information on known and un-known chemical entities 420. In FIG. 4C, the known chemical entity (+)-catechin, hereinafter referred to as simply "catechin", has been selected.

Referring again to the embodiment illustrated in FIG. 4A, library pane 406 displays information for the selected chemical entity catechin. There may be several kinds of information associated with chemical entity 420, which may be visually grouped into broad categories, such as information about the identity of the chemical entity 422, chromatography information for the chemical entity 424, and mass spectrometry information for the chemical entity, both in table form 426 and graph form 428.

FIG. 4D is a screen shot showing portions of library pane 406 in detail. Within the chemical identity information 422, a chemical entity's identity may include its compound name, Library ID, and Compound ID. In one embodiment, Library ID and compound ID are used to unambiguously identify the chemical entity within chemical library 126, while compound name is the informal or common name, used for readability. The Set Compound Name and Chemical Name fields are used to choose from among potentially multiple informal names. The Chemical Report Name and Library Report Name fields allow a user to choose which name will be used when the entity is referred to in generated chemical reports and library reports, respectively.

Chromatography information 424 for the chemical entity may include its retention time (RT) and retention index (RI), and may also include the RT window and RI window used during the identification process. For example, catechin had a retention time (RT) of 2.42 with a retention time window of 2, and a retention index (RI) of 2493 with a retention index window of 25. In the embodiment illustrated in FIG. 4D, the source of the information for the library entry is indicated in Group Name and Origin fields. Group Name identifies the particular analysis run which generated the data. An analysis run is herein referred to as an "injection", in reference to the act of injecting a sample of the substance to be analyzed into the input port of the chromatograph. Origin references the type of software used to create the entry and indicates that the data came from an actual analysis run, for example. The Confidence field indicates relative confidence that the chemical entity is actually what it has been identified to be. For example, a confidence value of 100 indicates a high confidence that the results recorded by the system and stored in the library entry are indicative of the chemical entity catechin. A confidence value may be set to 0, in which case the entry in chemical library 126 will not be considered during the matching process, i.e., the process by which a substance being analyzed is matched against potential candidates in chemical library 126.

As stated above, the subject matter described herein includes the ability to perform non-targeted analysis. This means that a chemical constituent may be detected and subsequently recognized, even though it may not be identified. In this case, Library ID and Compound ID fields will contain a value, but Compound Name field may be empty. A Confidence value of less than 100 may indicate that the mystery chemical entity has been unambiguously recognized but not yet identified.

FIG. 4E is a screen shot showing mass spectrometry information 426 in detail. The mass spectrometry information 426 may be organized visually into several tabs. In the embodiment illustrated in FIG. 4E, the "Mass" tab displays a mass information table containing mass spectrometry information collected during one or more injections. The "Public DB" tab displays information collected or available from public databases, which may contain a wide variety of information. For example, the Public DB tab may include mass spectrometry information collected or available from public MS databases, or other types of information from other public databases. The mass information table may include a list of the masses seen in primary scans, and may include not only the mass of the primary ion but also the mass of variants such as adducts (m+H, m+Na, 2 m+H), molecules containing isotopes (e.g., C-13, Cl-35, Cl-37), and expected or commonly occurring in-source fragments. In the embodiment illustrated in FIG. 4E, the mass information table includes information for multiple variants of catechin, one variant per row. The information displayed in FIG. 4E is primary MS data, but a plus sign ("+") on the left end of a row indicates that secondary MS data is also available. Viewing secondary MS data is described below, with reference to FIGS. 4G and 4H.

Variants use the following naming convention. A lower-case "m" symbolizes the chemical entity, while "m+H" symbolizes an ion created by attaching a proton, which is actually a hydrogen atom (atomic symbol "H") with the outer electron stripped off, to the chemical entity. An upper case "M" symbolizes either a fragment of or a compound including the chemical entity. For example, "M−151" refers to an in-source fragment of the chemical entity which has lost 151 atomic units worth of atoms from its molecular structure, while "M+16" refers to a compound comprising the chemical entity to which 16 atomic units worth of atoms has been added to its molecule. Symbols in square brackets indicate the presence of isotopes within the molecule. For example, "m+H[C13−1]" refers to an ion in which one carbon atom (atomic number 12) has been replaced with the carbon-13 isotope, and "m+H[C13−2]" refers to an ion in which two carbon atoms have been replaced with carbon-13 isotopes.

The information for each ion, shown as columns within each row, may include a mass column, showing the mass of the variant, and a mass window column. The mass window is the allowable error within the library entity that may be considered as a potential match to a detected chemical constituent. The mass ratio column indicates the relative proportion of a variant having one or more isotopes to the population as a whole. The 'Quant_mass' (quantized mass) column indicates which variants will have their masses included in the summary of information for the chemical entity (e.g., catechin). The weighting column is used during the matching process, allowing the user to fine-tune the sensitivity of the matching process. The name column is a descriptive field used to make the mass information more human-readable.

Figure 4F:
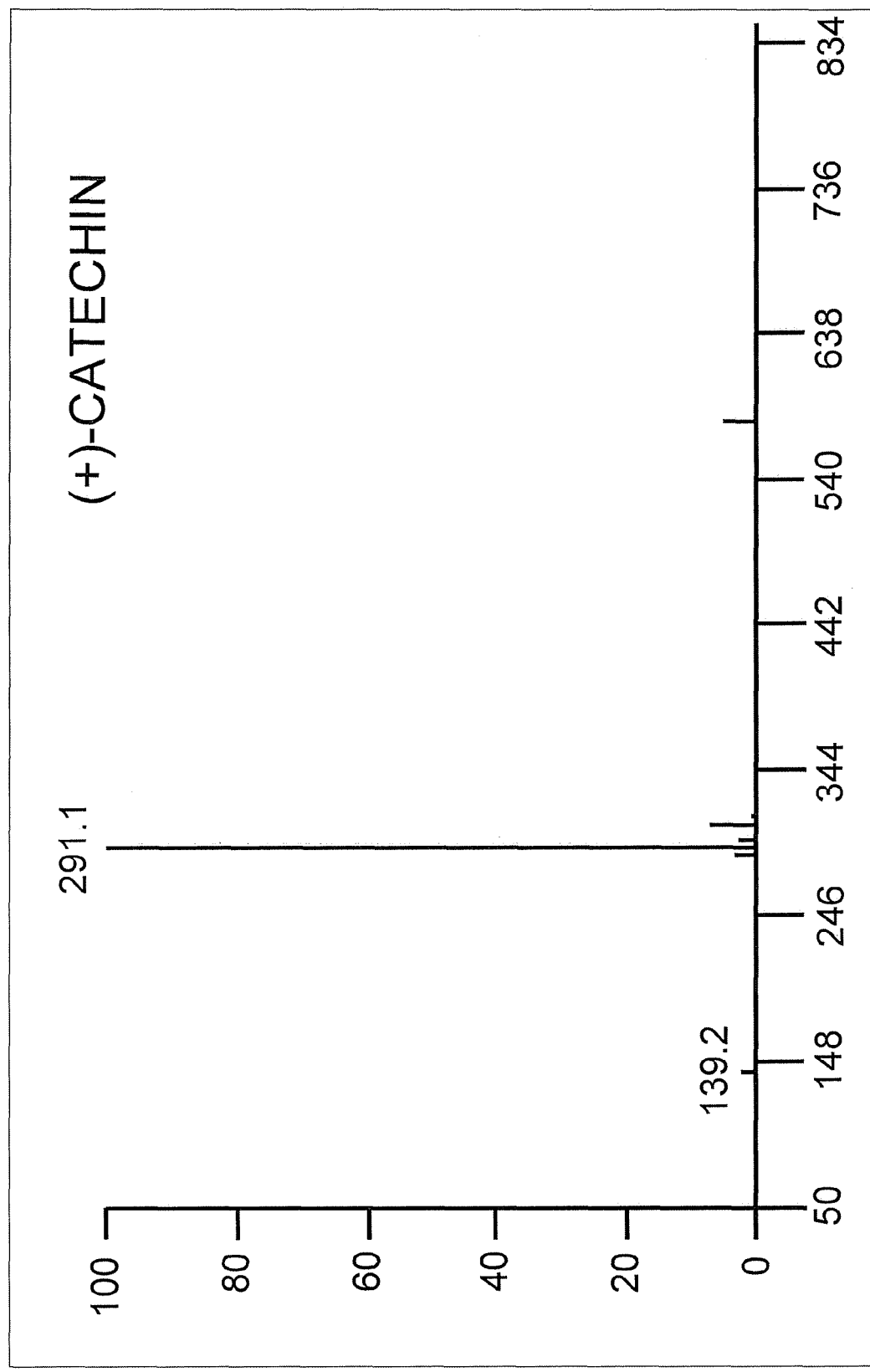

FIG. 4F is a screen shot showing mass spectometry information in graph form 428 in detail. In FIG. 4F, the relative intensities of the ions on the Y axis and mass on the X axis being obtained from the tabular data displayed in 426.

FIGS. 4G and 4H are screen shots showing more information about a library entry in chemical library 126 as displayed to a user via UI 128. In FIGS. 4G and 4H, primary MS data for an ion having a mass of 291.1 has been expanded to display the secondary MS data for that ion. In the embodiment illustrated in FIG. 4G, the plus sign on the left end of the top row has changed to a minus sign ("−") to indicate that the primary MS data has been expanded. Although only one level of secondary MS data is shown in FIG. 4G, higher-order MS data may also be available and so displayed. The mass information graph 428, shown in FIG. 4H, now shows the secondary MS data, in which two variants having a high mass ratio, one variant having a mass of 123.1 and the other having a mass of 139.1, can be seen as the two tallest peaks in the graph.

Figure 4J:
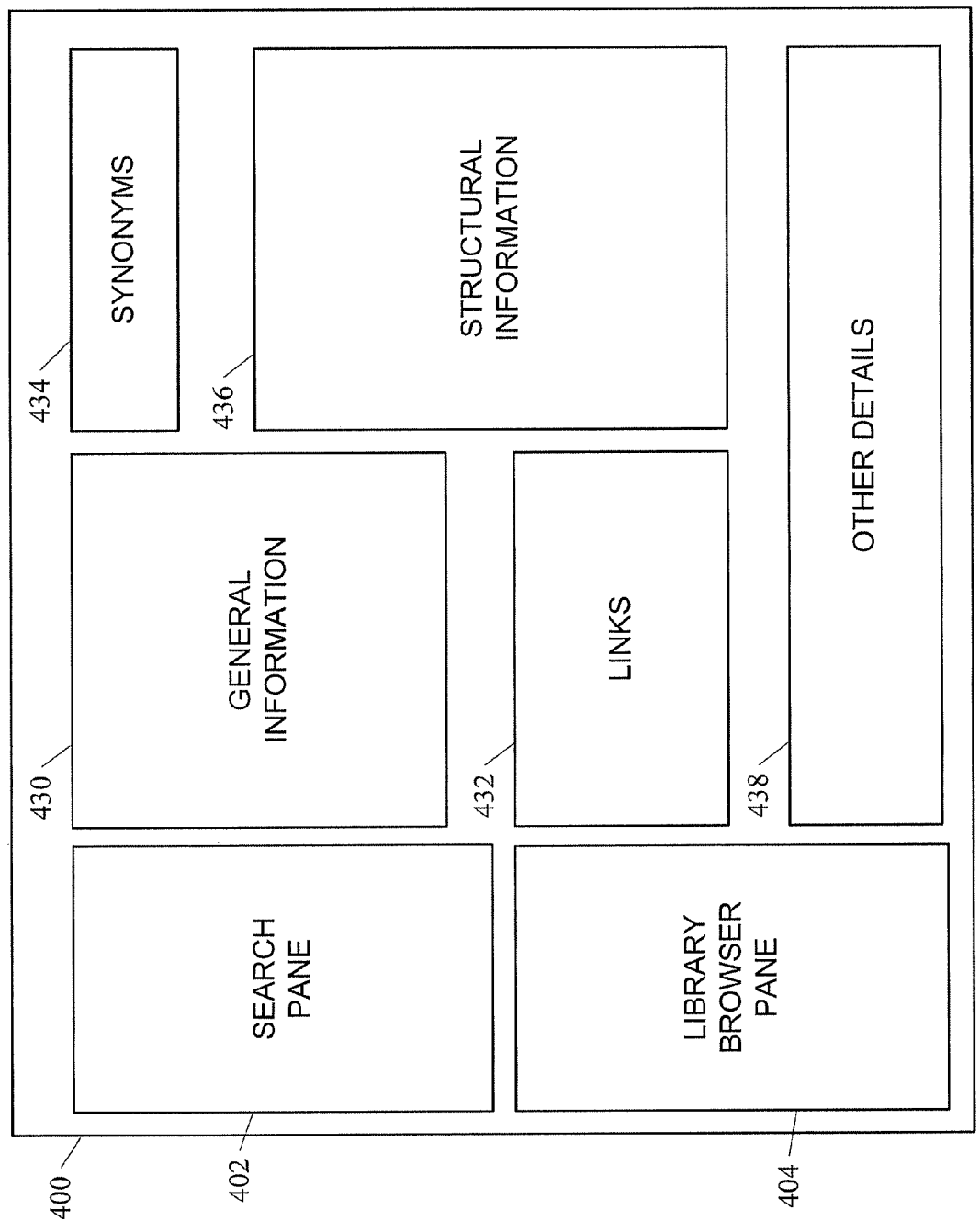
Figure 4M:
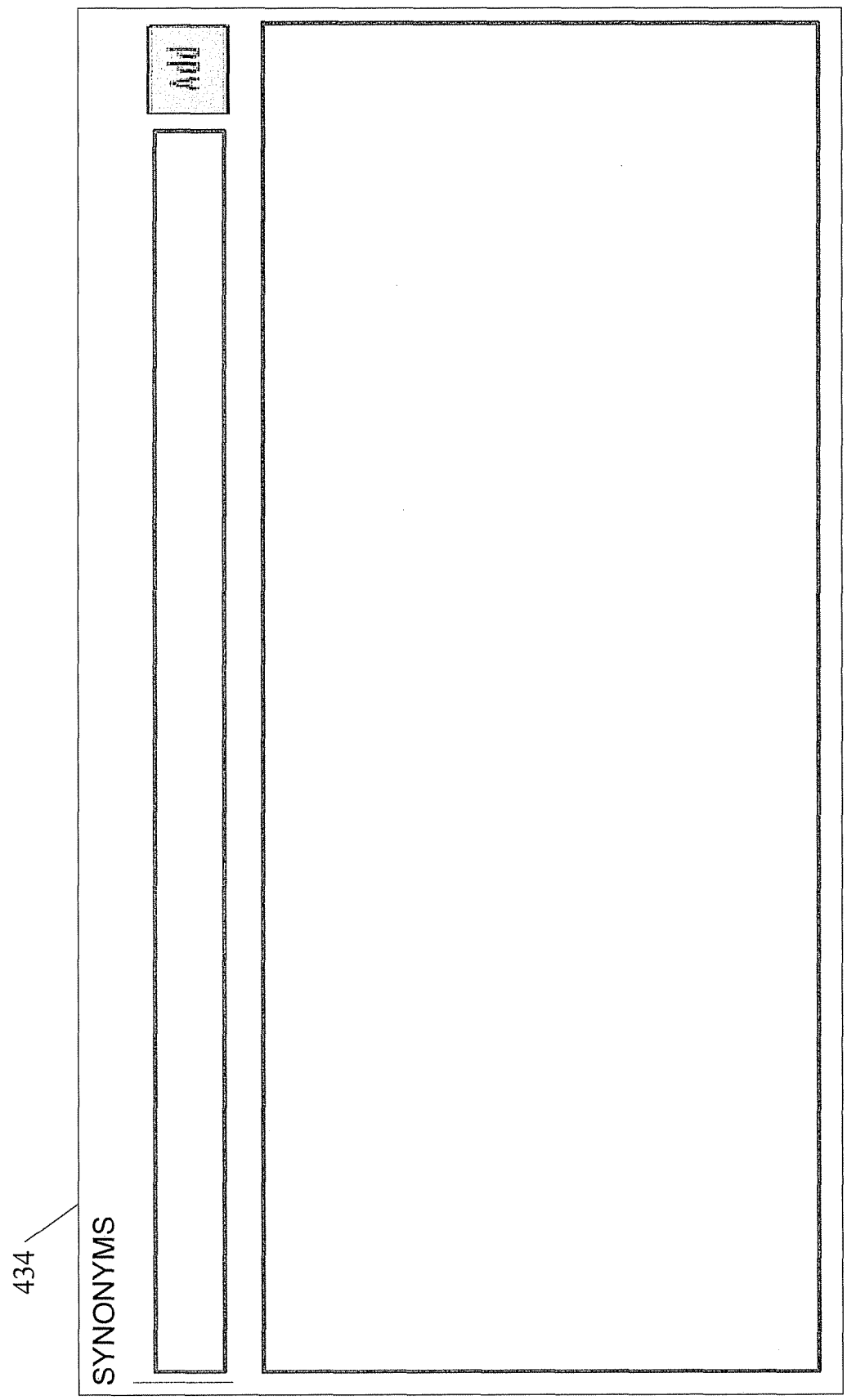
Figure 4N:
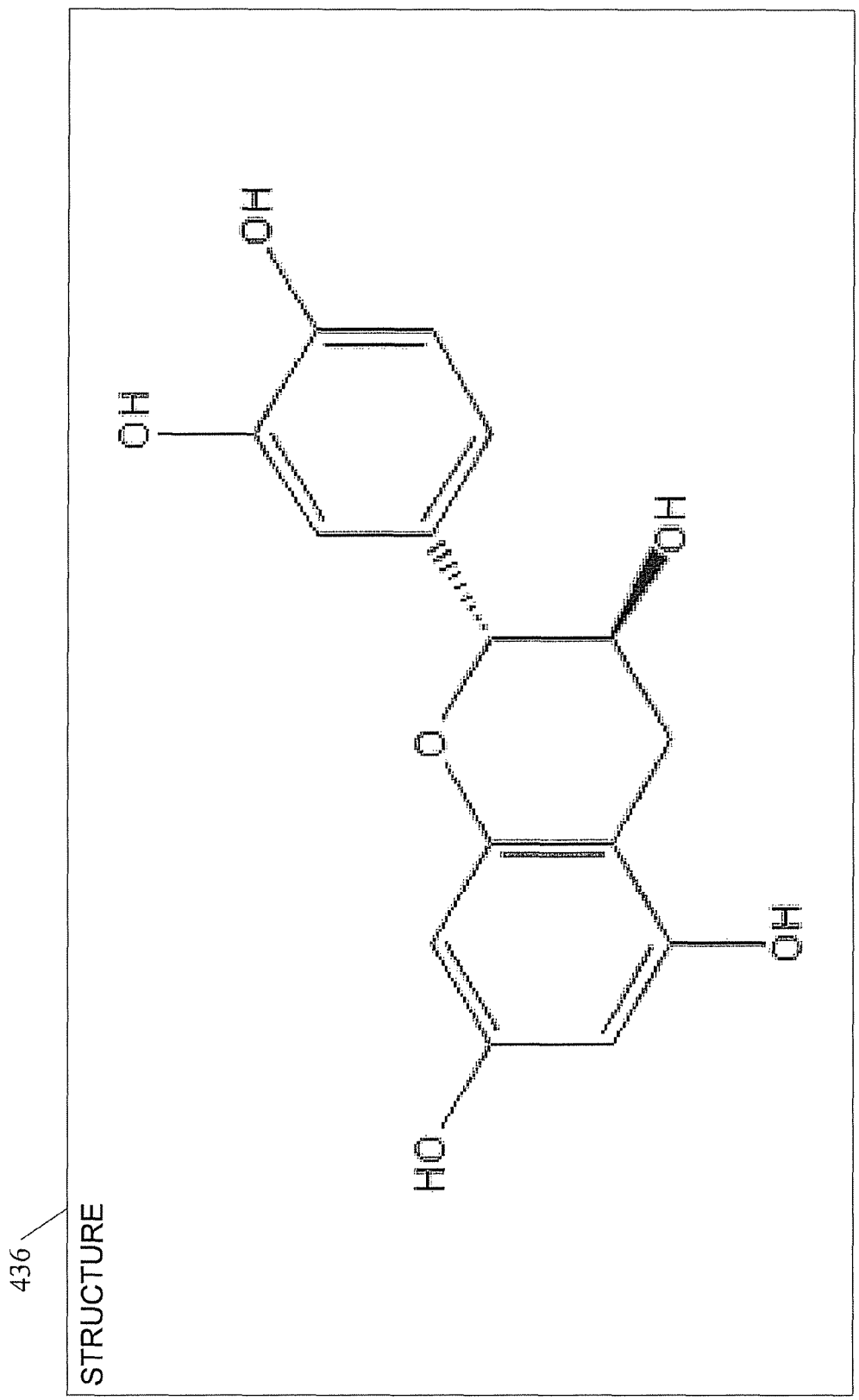

FIG. 4A displays information stored for entries in Library 412. FIG. 4J displays information stored for entries in Chemicals 408. In FIG. 4J, the functions of search pane 402 and library browser pane 404 are identical as described for FIG. 4A, and the description will not be repeated herein.

FIG. 4J is a screen shot showing structural information and physical properties associated with a molecule in chemical library 126. In one embodiment, an entry in Chemicals 408 may include general information 430 such as its chemical ID, chemical name, International Union of Pure and Applied Chemistry (IUPAC) name, classification, physical information and physical properties, and chemical details such as molecular formula, shown in more detail in FIG. 4K. Chemicals 408 may include links 432 for cross-referencing the chemical entity to information in Library 412 and Public DB 410, shown in more detail in FIG. 4L. An entry in Chemicals 408 may include synonyms 434 for the chemical entity, shown in more detail in FIG. 4M, and may contain structural information 436, such as a molecular diagram of the molecule, shown in more detail in FIG. 4N. The user may also be presented with other details 438, such as lists of physical stocks from which the substance may be obtained, annotations, keywords which can be used as search terms, and any other kind of information that may be included as an attachment, shown in more detail in FIG. 4P.

FIGS. 4A through 4P illustrate the kinds of information stored in chemical library 126 that may be viewed and browsed by a user. FIGS. 4Q through 4W and FIGS. 5A through 5E show how a user might use the system to compare data recorded for a sample undergoing analysis with chemical library 126 entities, either during a manual matching step or in order to review the results of an automatic matching algorithm.

Figure 4Q:
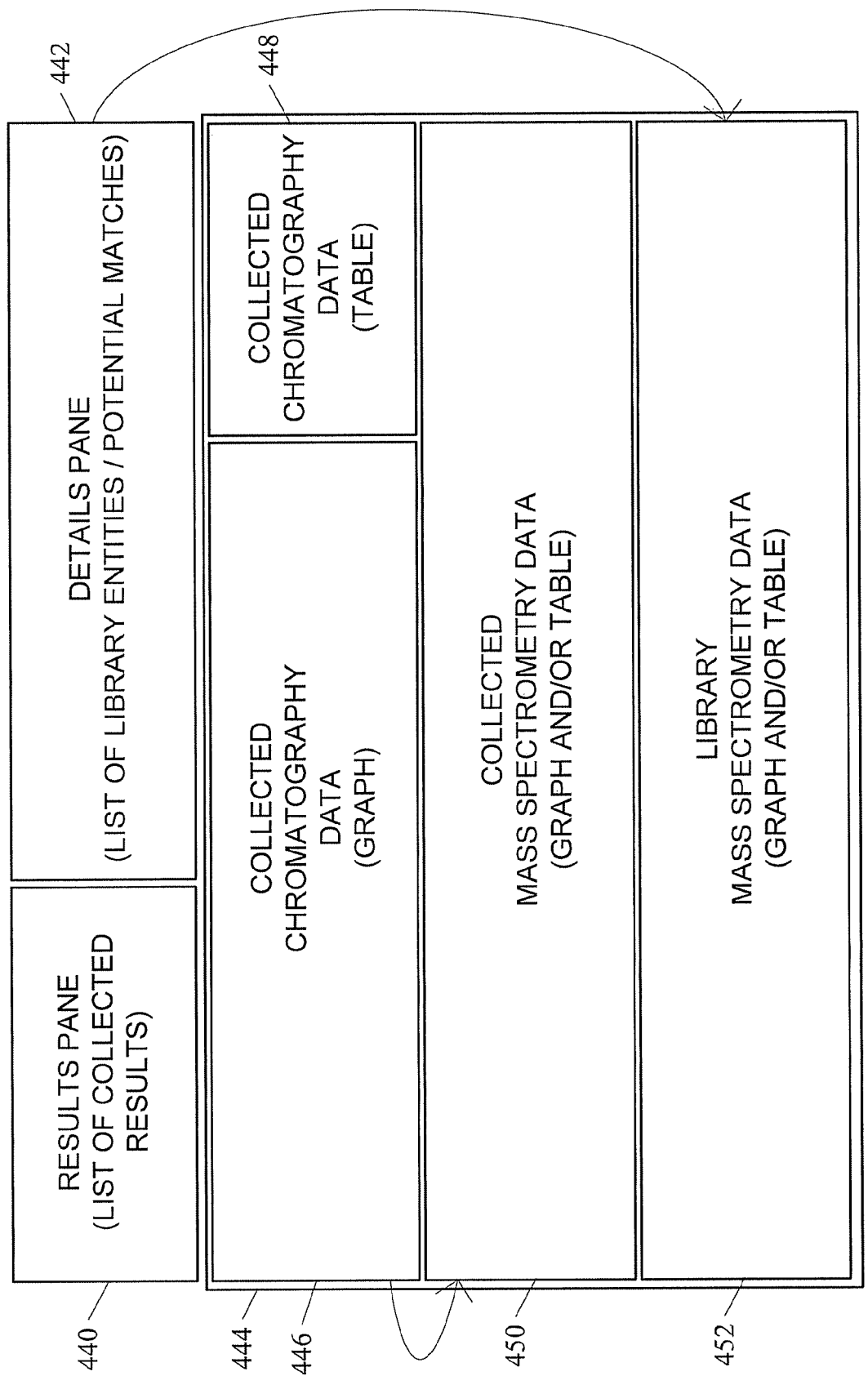

FIG. 4Q represents information that may be presented to a user via GUI 128, according to an embodiment of the subject matter described herein. In FIG. 4Q, a user may be presented with results data collected from one or more injections. In one embodiment, a results pane 440, shown in more detail in FIG. 4R, provides a scrolling list of injections that were performed, showing sample name, date that the data was acquired (e.g., the date that the injection was performed), the name of the file containing information associated with the injection, client ID, and other information associated with a particular injection. Referring to FIG. 4Q, graph pane 444 may include a details pane 442 and a graph pane 444. Referring to the embodiment of results page 440 illustrated in FIG. 4R, the top row visible in the list is selected, and the data associated with that injection is displayed in tabular form in the details pane 442 and in graphic form in the graph pane 444 occupying the lower ¾ths of FIG. 4Q. As the user scrolls through the list of injections in results pane 440 the data displayed in details pane 442 and graph pane 444 will change accordingly, to display data associated with the injection currently selected within results pane 440.

Figure 4S:
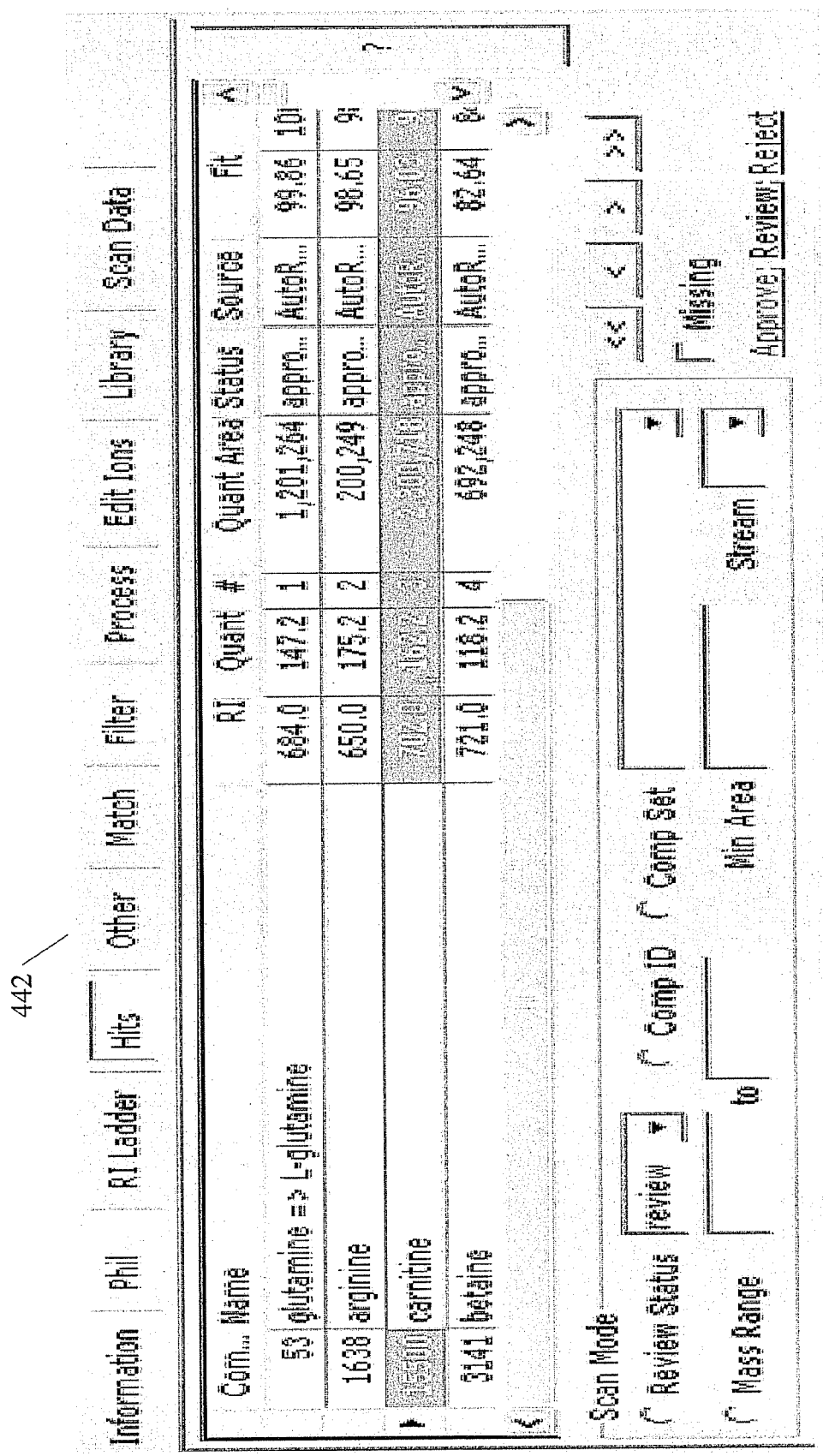

FIG. 4S is a screen shot of details pane 442 in detail. In one embodiment, details pane 442 may include a series of tabs for organizing the data associated with the injection and displaying the associated data to the user in user-comprehensible form or in a form that enhances that user's ability to understand, absorb, and use the data. In the embodiment illustrated in FIG. 4S, details pane 442 currently displays the "Hits" tab, which presents to the user a list of the chemical entities that the matching algorithm has determined to best match the chromatography and mass spectrometry data collected for that injection, herein referred to as the "injection data". In other words, the Hits tab displays the system's best guess as to the identity of components within sample being analyzed. In one embodiment, this list of likely components may be presented in a table form, listing the name of the chemical entity along with its chromatography and mass spectrometry data.

In one embodiment, in response to selection of one of the injections listed in results pane 440, system 100 may display the injection data in graph pane 444. In one embodiment, graph pane 444 may display all or only a portion of the injection data. For example, graph pane 444 may display only the subset of injection data upon which the matching algorithm based its determination of the identity of the selected component within details pane 442. In the embodiment illustrated in FIG. 4Q, graph pane 444 contains three separate graphs.

Figure 4T:
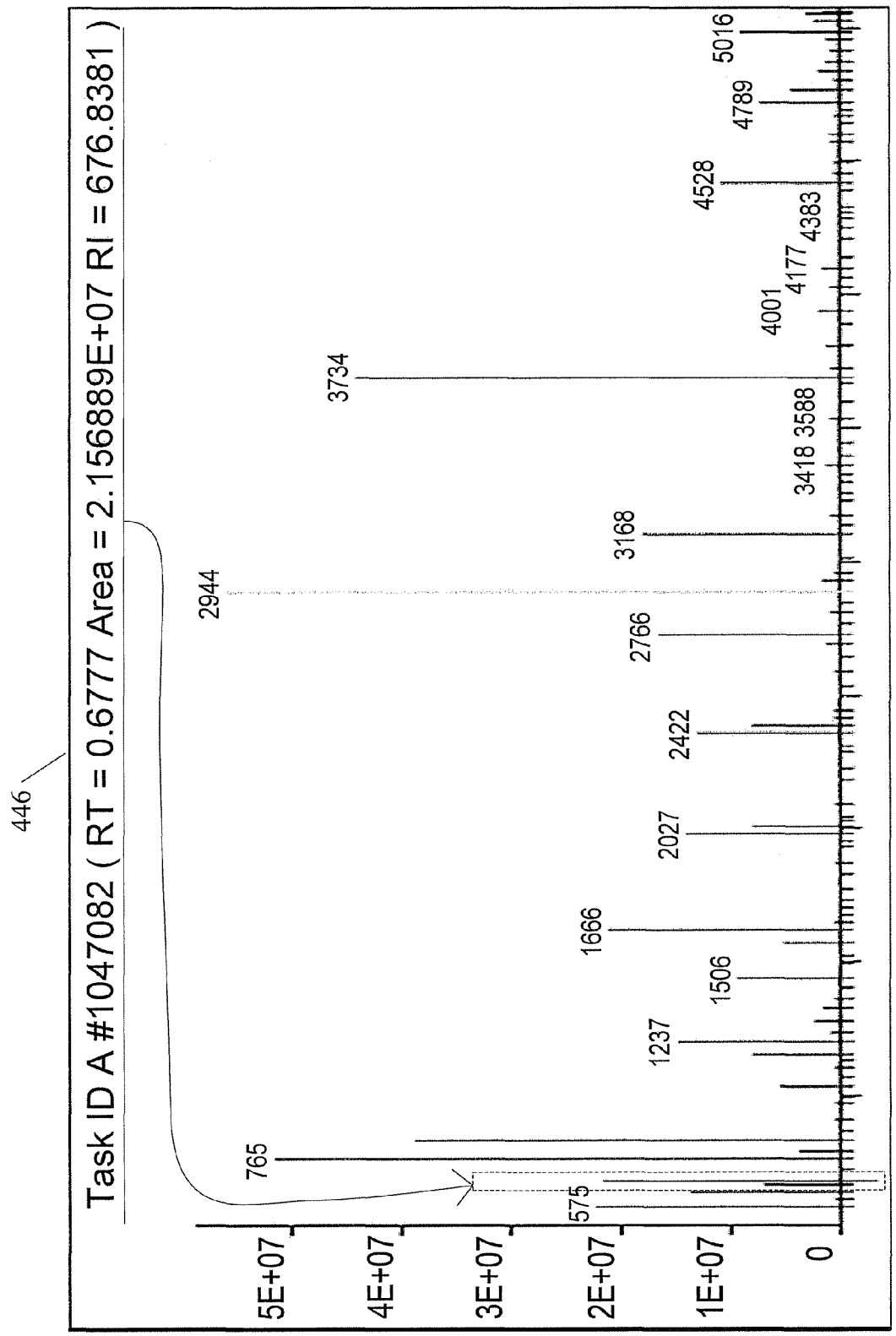

The top graph 446 displays a graph of the chromatography data for the injection selected in results pane 440, with retention time or retention index as the X axis and intensity as the Y axis. FIG. 4T is a screen shot of top graph 446 in detail. Referring to FIG. 4T, top graph 446 displays the chromatography data in the form of components. A component is a stick which represents a collection of chromatographic peaks with similar chromatographic properties. For example, a component may contain one or more unrelated substances that co-elute. Top graph 446 does not display any information about the masses contained in the components that eluted at a particular retention time.

Referring again to FIG. 4R, in one embodiment, the user may opt to display the information in table form 448, as shown in more detail in FIG. 4U. Presenting the same information in table form allows the user to see the peak information in more detail, and may allow the user to detect peaks otherwise too small to distinguish in the graph form. Although top graph 446 presents the peaks as idealized columns of fixed width, the raw chromatography data may be a peak with a shape, including height, width of base, and area. These details may be included in the table form 448 of the data. Referring to FIG. 4T, the title of top graph 446 indicates that a component at RT=0.6777 has been selected. This is also reflected in table form 448, in which the information at RT=0.68 has been selected.

Figure 4V:
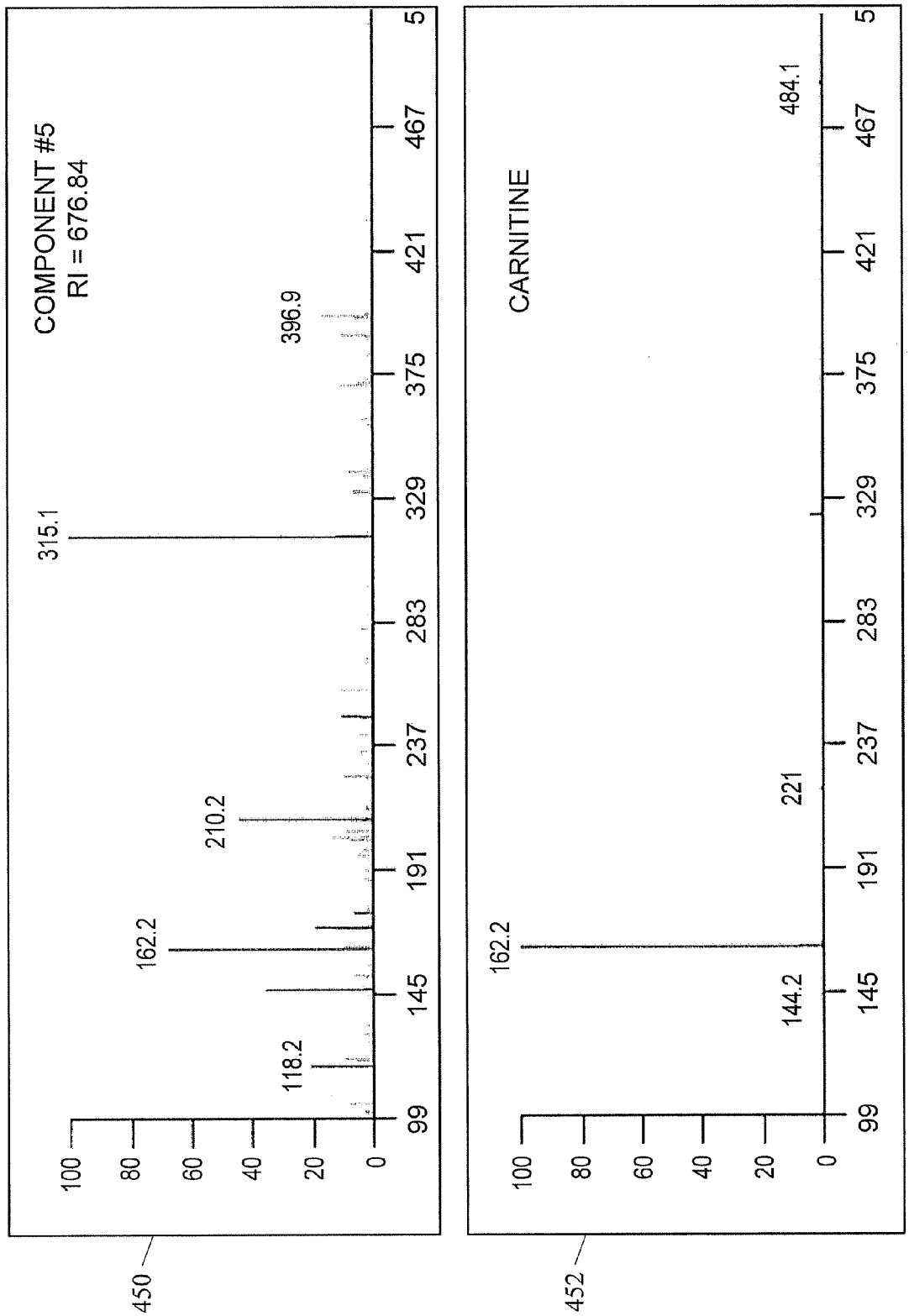

In the embodiment illustrated in FIG. 4Q, a middle graph 450 may show primary MS data for a particular component or retention time window, and a bottom graph 452 may show primary MS data for an entry in chemical library 126. FIG. 4V is a screen shot of a portion of graph pane 444 in detail. In FIG. 4V, the title displayed at the top of middle graph 450 indicates that middle graph 450 shows mass spectrometry data for the fifth component. Middle graph 450 displays primary MS data for this fifth component, with mass on the X axis and relative intensity on the Y axis. As the user scrolls from component to component through the chromatography data shown in top graph 446, the contents of middle graph 450 will change to display the primary MS data for the component currently selected in top graph 446. This in turn will cause 442 to display 'hits' and 452 to show matching Library information.

Like the primary MS data displayed in middle graph 450, bottom graph 452 displays a graph with mass on the X axis and relative intensity on the Y axis. In this example, one of the "hits" listed in details pane 442 has been selected, either automatically or by the user, in this case the chemical entity carnitine. In bottom graph 452, MS data for the chemical entity carnitine is shown, as can be seen by the title displayed at the top of bottom graph 452. Carnitine may have been selected by the matching algorithm as the most likely candidate for the substance that eluted at RT=0.6777, or the user may have manually selected carnitine. The user may thus compare the data collected during the injection in middle graph 450 to the primary data from the library entry in bottom graph 452, either to verify the accuracy of the matching results or to perform manual matching of primary MS data from the injection to primary MS data associated with an entity in chemical library 126.

Although the embodiment illustrated in FIG. 4Q shows data in table form only for top graph 446, in one embodiment, data may be displayed in table form for any graph, including middle graph 450 and bottom graph 452. Furthermore, graph pane 444 may contain any number of graphs, and is not limited to only three graphs as illustrated in FIG. 4Q.

In one embodiment, peak data within the primary MS data displayed in middle graph 450 may be color coded to indicate to the user that secondary MS data is available. The user may select the peak, such as by clicking on a peak within the primary MS data shown in middle graph 450, selecting an entry from data displayed in table form, etc. In response, system 100 may display the secondary MS data associated with the selected peak in the primary MS data. In the embodiment illustrated in FIG. 4D, the primary MS data for component #5 includes several peaks representing substances of various masses, the component represented by the vertical bar having a retention time of 0.6777. In this example, the peak indicating the presence of an ion having a mass of 162.2 has associate with it secondary MS data. A user may thus "drill down" on this peak to show the secondary MS data. An example of this is shown in FIG. 4W.

In one embodiment, selection of a primary MS peak may trigger system 100 to display secondary MS data already collected for that peak. For example, the user may use UI 128 to identify a peak for which the user desires to see information from chemical library 126. In the embodiment illustrated in FIG. 4W, middle graph 450 displays secondary MS data associated with the ion having a mass of 162.2 at retention time 0.7046 in the primary MS, as can be seen in the title at the top of middle graph 450. Bottom graph 452 displays the secondary MS data associated with corresponding ion, i.e., having a mass of 162.2, of the entity selected from chemical library 126.

In one embodiment, in this manner the user selects a chromatography peak displayed in top graph 444, which causes the primary MS data for that chromatography peak to be displayed in middle graph 450. A user may then select a primary MS peak in middle graph 450, which causes the secondary MS data for that primary MS peak to be displayed in middle graph 450. At the same time, system 100 may display the corresponding entity in chemical library 126 in bottom graph 452. When middle graph 450 displays primary MS data for an injection, bottom graph 452 may display primary MS data for an entry in chemical library 126. When middle graph 450 displays secondary MS data for an injection, bottom graph 452 may display secondary MS data for the entry in chemical library 126. As the user scrolls through the data in middle graph 450, the data displayed in bottom graph 452 changes. In other words, in one embodiment, middle graph 450 and bottom graph 452 are synchronized, where a change in middle graph 450 causes a corresponding change in bottom graph 452. In this manner, as a user navigates through the injection data, system 100 may automatically display pertinent data from the library.

Figure 4W:
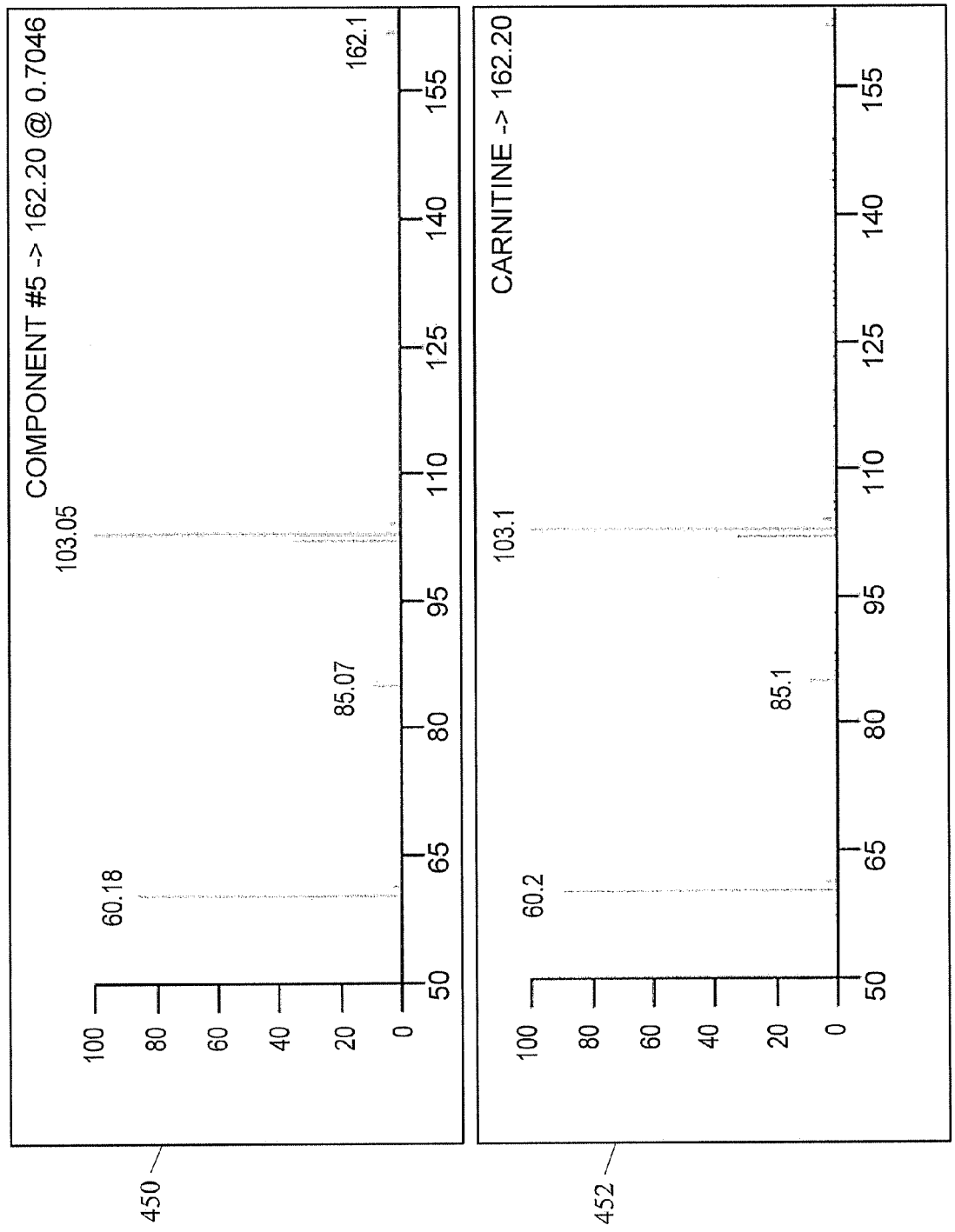

Although only two levels of MS data are displayed in FIGS. 4V and 4W, the same concept may be extended to allow the user to generate and/or access higher orders of MS data, and is not limited to primary and secondary MS data only. In one embodiment, a user may access $MS^n$ data via mouse, menu, or scroll wheel.

In one embodiment, a user may use a mouse to click on a peak in any of the results graphs, causing system 100 to display the equivalent library information for a chemical entity of that known location on the graph. In one example, a user may see a peak having a retention index of X; the user may click on the peak, triggering system 100 to record the value of the retention index, identify entities within its chemical inventory having the same retention index, and display the information for those identified entities in its chemical inventory. Thus, a user may use UI 128 to navigate the data collected for the injection, including chromatographic data, primary MS data, and secondary MS data, and may use UI 128 to navigate through entries in chemical library 126, either to manually match library entries to injection results or to verify the results of the matching process.

In FIGS. 4A–4W, the underlying chromatography and mass spectrometry data peaks are represented as idealized peaks or bars having height and minimum or no width. However, the raw chromatography or mass spectrometry data describes a peak having a shape and area. In one embodiment, a user may access the raw peak data. For example, UI 128 may be configured so that if the user positions the mouse or other pointing device over an entity, either a peak in a graph or a row in a table, a pop-up window may be displayed containing detailed information about that entity. This is shown in FIG. 5A.

Figure 5A:
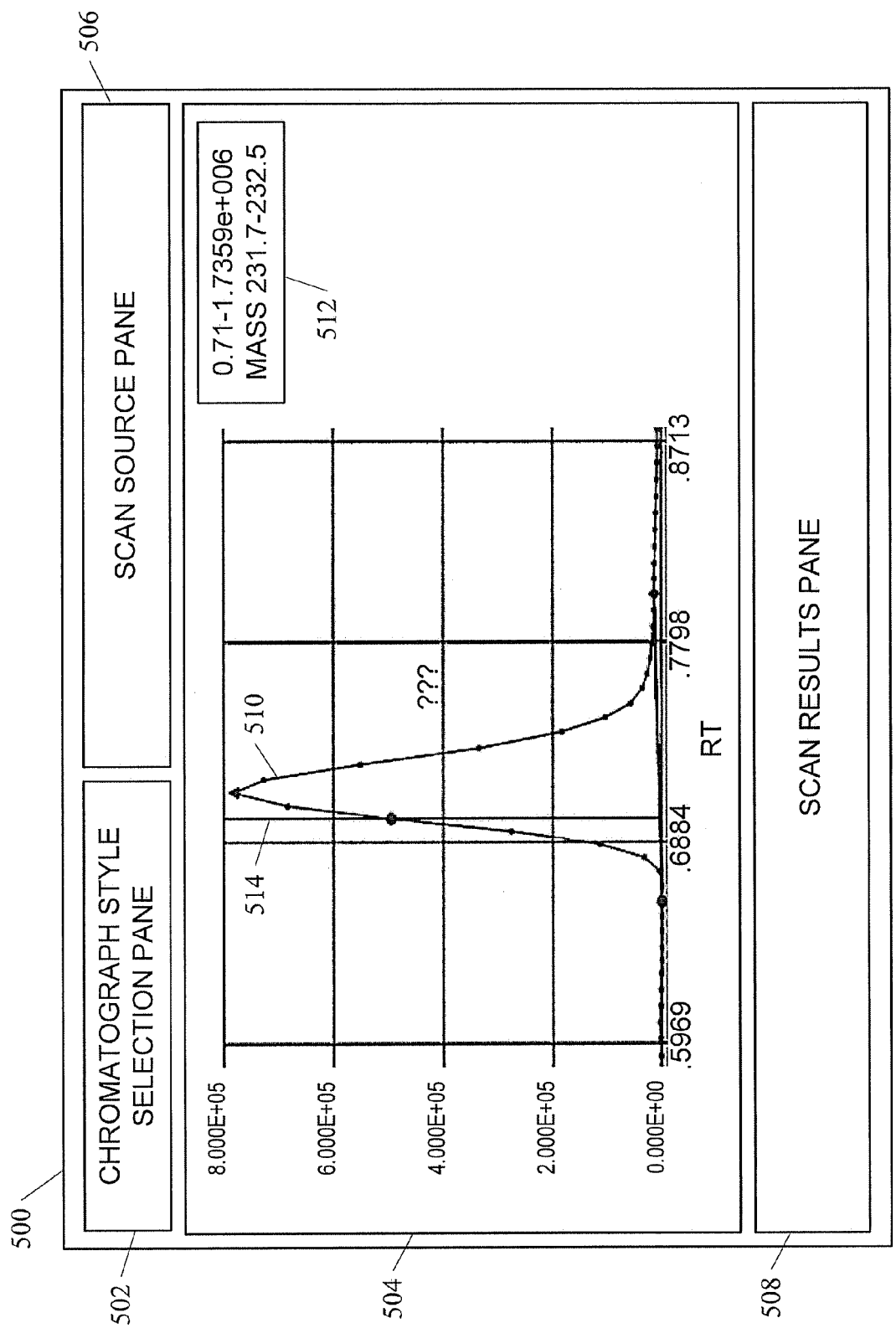
Figure 5B:
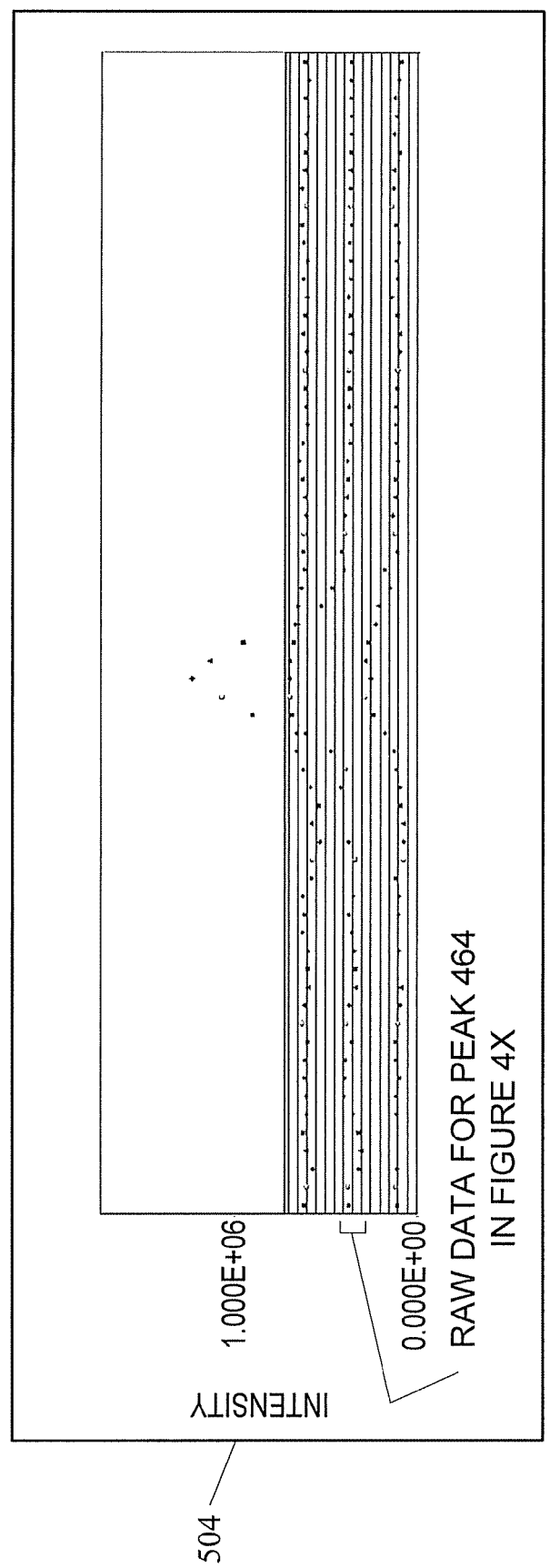
Figure 5C:
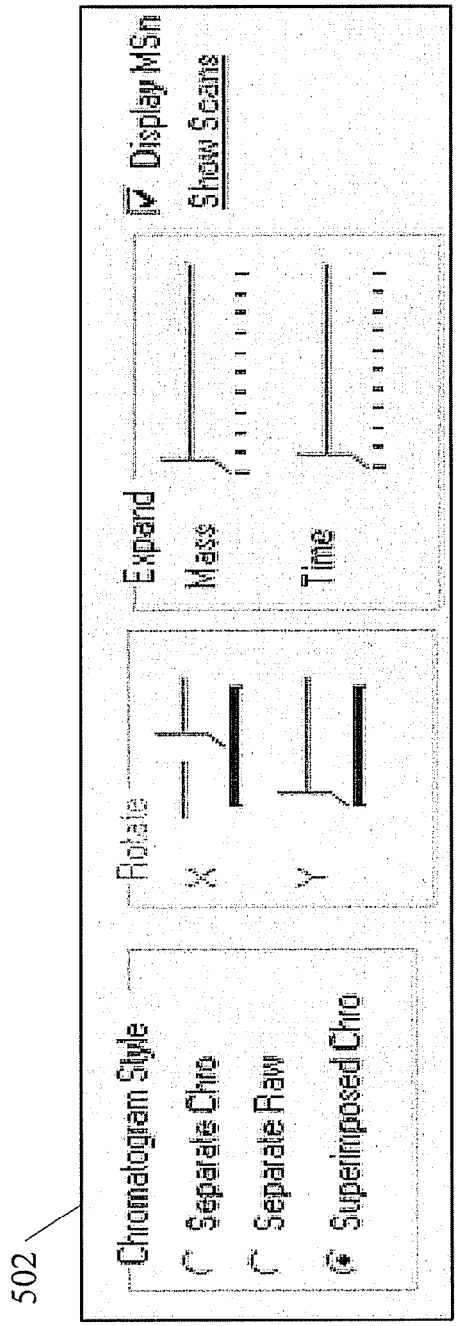

FIG. 5A is a screen shot showing detailed separation (e.g., chromatogram) data, referred to hereinafter as "peak" data. In FIG. 5A, the window 500, titled "ScanViewer", shows the shape of the actual peak detected during one injection, shown in peak display pane 504. In this manner, the user may see detailed peak information, not just a line representing the peak intensity and retention time. Within the scan viewer window 500, chromatogram style selection box 502 allows a user to choose how the peak data is displayed. The user may show peak data for all masses detected or for a subset of masses detected. In one embodiment, the user may display peaks of interest as separate peaks, each in a separate graph or graph window ("Separate Chro"), each graph representing a different m/z value or range of m/z values. Alternatively, the user may display a single graph in which the peaks having different m/z values are superimposed over each other in one graph or graph window ("Separate Chro"), as shown in FIG. 5A. The user may also view the raw data collected ("Separate Raw to give the "), as shown in FIG. 5B. FIG. 5C is a screen shot showing chromatogram style selection box 502 in more detail.

Figure 5D:
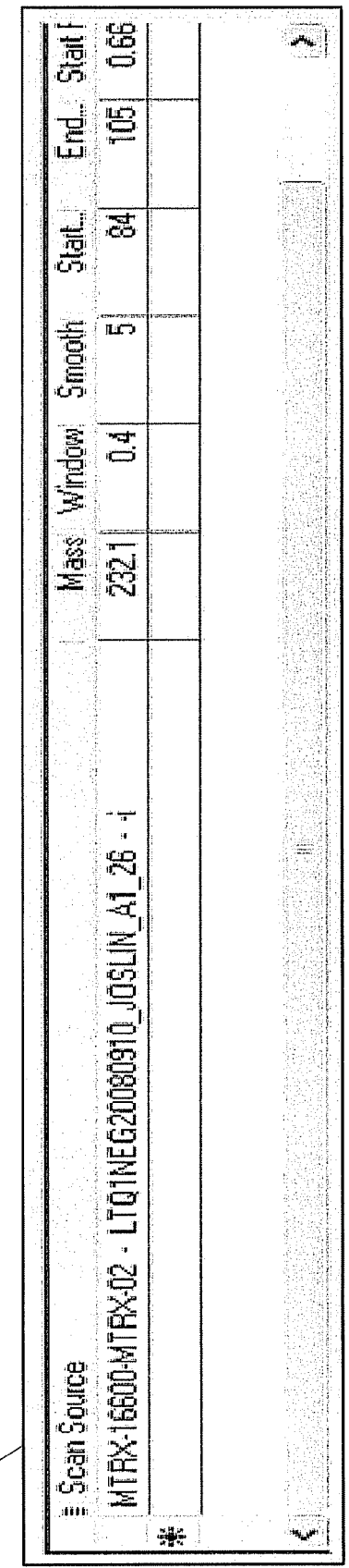

In the embodiment illustrated in FIG. 5A, a scan source pane 506 displays the source of the scans from which the peak data is collected and displayed. FIG. 5D is a screen shot showing scan source pane 506 in more detail. The user may select multiple scan sources as the source for the peak data.

Figure 5E:
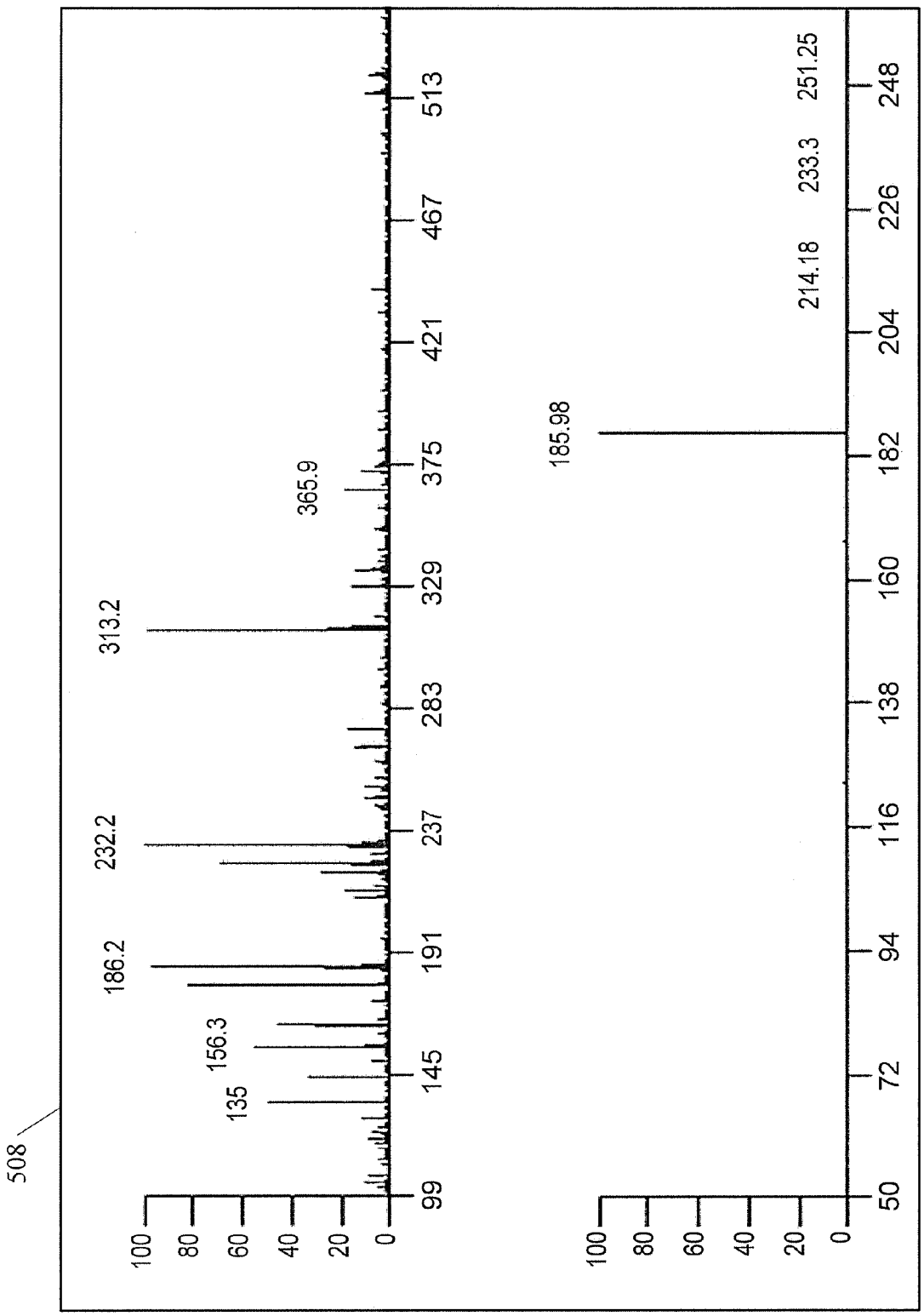

Referring to FIG. 5A, at the bottom of window 500, scan results pane 508 shows all of the ions that represent ions in a scan. FIG. 5E is a screen shot showing scan results pane 508 in detail. In one embodiment, this list of scans may be selected by the user from a set of chromatographic peaks displayed in middle graph 450, or they may be selected by software. Data for a particular peak or peaks is displayed in peak display pane 504. In the embodiment illustrated in FIG. 5A, peak display pane 504 displays a single peak 510. Symbols on peak 510 indicate peak start, peak apex, and peak end. A point on peak 510 may indicate, using a different point shape, color coding, or other visual means, the availability of secondary MS data, or that the secondary MS data for that point was the secondary MS data used during the matching process to identify the chemical constituent.

A legend 512 in the upper right-hand corner of the peak display pane indicates information for the part of the graph indicated by the cursor 514, which is the vertical line intersecting chromatographic peak 510. In the example shown in FIG. 5A, legend 512 indicates that the chromatographic peak marked by cursor 514 is positioned at 0.71 RT, and that the area for chromatographic peak 510 is 1.7349e+006. Legend 512 also indicates that peak 510 includes masses in the range of 231.7 to 232.5 AMUs. Thus, the user is informed that peak 510 shown in FIG. 5A may represent ions having different masses but measured in primary scans that where collected in a region of time near the peak. If the user selects a point on peak 510 using cursor 514, the primary MS data will be displayed in the top half of scan results pane 508. If secondary MS data is also available, the secondary MS data may be displayed in the bottom half of scan results pane 508.

Although FIG. 5A shows ScanViewer operating in "Superimposed Chromatogram" mode, the data window defined by the user (i.e., the boundaries of which are determined by values in the "Mass", "Window", "Start" and "End" columns in table 506) includes only one peak, seen as peak 510. Had the data window been large enough to include additional chromatography peaks, display pane 504 would display the additional peaks present within the specified data window in the data source or sources listed in table 506.

FIG. 5B is a screen shot illustrating an example of peak data displayed using the "Separate Raw" mode. displays a graph of the raw peak data recorded, including data for the peak shown in FIG. 5A. The data points shown in FIG. 5B can be visually organized into three sets or horizontal rows of data points. The middle of the three horizontal sets of data points are the raw data from which peak 510 in FIG. 5A was derived. The top and bottom horizontal sets of data points were not included within the data window specified in FIG. 5A.

The graph includes three dimensions: retention time in the X axis, intensity in the Y axis, and mass in the Z axis. From the graph in FIG. 5B it can be seen that the single peak in FIG. 5A, which was limited to a mass range of 231.7~232.5, represents primarily only one ion having a mass of approximately 232 (the middle series of points spanning the graph from left to right). However, the graph in FIG. 5B shows that two other ions were eluted at the same time, having masses of approximately 231 and 233, respectively (the top and bottom series of points spanning the graph from left to right). Thus, using this window, a user may look at data in a different time scale, or change the range of masses that should be included in a particular peak. For example, a user may decide that data for the ions having masses of 231 and 233 should also be included in the peak data of FIG. 5A. Alternatively, the user may determine that several ions were combined into a single peak by the peak detection algorithm, and instruct the peak detection algorithm to exclude some of those ions as spurious, by changing the mass range for a particular peak. In short, not only may the user have direct access to the raw injection data, the user may use that information to fine-tune the decisions made by the matching algorithm.

It will be understood that various details of the subject matter described herein may be changed without departing from the scope of the subject matter described herein. Furthermore, the foregoing description is for the purpose of illustration only, and not for the purpose of limitation.

What is claimed is:

1. A method for non-targeted determination of composition of chemical constituents in a complex mixture, the method comprising:
    generating, using a separation technique and a mass spectrometer, separation and mass spectrometry data of a sample, wherein the separation data includes peak information and wherein the mass spectrometry data includes primary and secondary mass spectrometry data;
    collecting and storing analysis results, the analysis results including the generated separation and mass spectrometry data;
    determining a chemical constituent of the sample by comparison of the analysis results to a library of information indicating characteristics of chemical entities, wherein the comparison is based on the separation and mass spectrometry data, wherein the library of information comprises data generated by the separation technique and mass spectrometer, and wherein the library of information includes separation and mass spectrometry data for identified and unidentified chemical entities; and
    making available in human-accessible form an indication of the chemical constituent of the sample.

2. The method of claim 1 wherein using a separation technique to generate separation data of a sample includes using a chromatograph to generate chromatography data of a sample and wherein the separation information includes retention information.

3. The method of claim 2 wherein using a chromatograph to generate chromatography data of a sample includes using a ultra-high pressure liquid chromatograph.

4. The method of claim 2 wherein the retention information comprises at least one of a retention time of a peak and a retention index of a peak.

5. The method of claim 1 wherein using a separation technique to generate separation data of a sample includes using electrophoresis and wherein the separation information includes separation distance information.

6. The method of claim 1 wherein using a mass spectrometer to generate mass spectrometry data of a sample includes using a quadrupole mass spectrometer.

7. The method of claim 1 wherein using a mass spectrometer to generate mass spectrometry data of a sample includes using a mass spectrometer having an ion trap.

8. The method of claim 1 wherein using a separation technique and a mass spectrometer to generate separation and mass spectrometry data of a sample includes generating separation and mass spectrometry data for a plurality of samples, and wherein collecting the analysis results includes collecting separation and mass spectrometry data generated for the plurality of samples.

9. The method of claim 1 wherein generating the separation and mass spectrometry data includes at least one of:
    performing a acidic liquid chromatography;
    performing a basic liquid chromatography;
    performing a positive ion mass spectrometry;
    performing a negative ion mass spectrometry;
    performing a plurality of separations; and
    performing a plurality of mass spectrometries.

10. The method of claim 1 wherein the peak information comprises at least one of:
    an intensity of a peak;
    a width of the base of a peak;
    a retention time of the start and end of the base of a peak;
    an intensity of the start and end of the base of a peak;
    a width of a peak at half of the peak's height;
    an area of a peak;
    a symmetry of a peak;
    a noise of a peak;
    a mass associated with a peak;
    a mass-to-charge ratio associated with a peak;
    an association of a peak to an entity in an ion tree describing parent-child relationships between ions; and
    a list of scans associated with a peak.

11. The method of claim 1 wherein storing the analysis results includes storing information describing the nature of the analysis results, wherein the information describing the nature of the analysis results includes at least one of:

a number of primary scans taken during an analysis;
a number of secondary scans taken during an analysis;
a percentage of secondary scans actually taken versus secondary scans that could have been taken;
a number of secondary scans taken that were within the peak of an identified chemical entity;
a percentage of secondary scans taken that were within the peak of an identified chemical entity;
a number of peaks recorded during an analysis;
a number of peaks for which a secondary scan has been taken;
a percentage of peaks for which a secondary scan has been taken;
a number of peaks that have more than one secondary scan associated with the peak;
a percentage of peaks that have more than one secondary scan associated with the peak;
an area of the largest peak for which a secondary scan was not performed; and
an area of the smallest peak for which a secondary scan was performed.

12. The method of claim 1 wherein storing the analysis results includes storing the analysis results in a database.

13. The method of claim 1 wherein comparing the analysis results to the library of information includes comparing the analysis results to information stored in a database for storing the library of information.

14. The method of claim 1 wherein comparison of the analysis results to a library of information includes comparison of the analysis results to a characteristic of an entity within the library, including a comparison of at least one of:
   a retention time of the entity;
   a retention index of the entity;
   a mass of the entity;
   a mass-to-charge ratio for the entity;
   a mass of an adduct of the entity;
   an isotope relationship of the entity;
   a mass of a fragment of the entity;
   a relationship of the entity to the entity's child ions;
   a relationship of the entity to the entity's parent entity;
   a relationship of the entity to a sibling of the entity;
   relative intensity of the entity;
   structural information for the entity;
   physical properties of the entity;
   a list of physical stocks of the entity;
   information available within a public chemical database entry for the entity;
   information about the entity available within a second library of information; and
   analysis results associated with the entity.

15. The method of claim 1 wherein determining the composition of the sample includes displaying the analysis results and library information for a particular entity in the library.

16. The method of claim 1 comprising storing, in the library of information, information about detected but unidentified chemical entities identified as present in the sample.

17. The method of claim 1 comprising using a user interface coupled to the analysis module for displaying the analysis results and library information for a particular entity in the library.

18. The method of claim 1 wherein generating the separation data includes using one of ion-mobility spectrometry and capillary electrophoresis.

19. A system for non-targeted determination of composition of chemical constituents in a complex mixture, the system comprising:
   a separation tool for performing separations of chemical constituents of a sample and generating separation data, wherein the separation data includes peak information;
   a mass spectrometer for performing mass spectrometry on portions of the separated chemical constituents of the sample and generating mass spectrometry data, wherein the mass spectrometry data includes primary and secondary mass spectrometry data;
   a library of information indicating characteristics of chemical entities, wherein the library of information comprises data generated by the separation tool and mass spectrometer and wherein the library of information includes separation and mass spectrometry data for identified and unidentified chemical entities;
   an analysis module for receiving and collecting and storing as analysis results the separation and mass spectrometry data and for determining a chemical constituent of the sample by comparison of the analysis results to the library of information, wherein the comparison is based on the separation and mass spectrometry data; and
   a user interface, coupled to the analysis module, for making available in human-accessible form an indication of the chemical constituent of the sample.

20. The system of claim 19 wherein the separation tool comprises a chromatograph.

21. The system of claim 20 wherein the chromatograph comprises a liquid chromatograph.

22. The system of claim 21 comprising an electrospray ionization device for coupling the liquid chromatograph to the mass spectrometer.

23. The system of claim 21 wherein the liquid chromatograph comprises an ultra-high pressure liquid chromatograph.

24. The system of claim 20 wherein the chromatograph comprises a gas chromatograph.

25. The system of claim 19 wherein the separation tool comprises an electrophoresis tool.

26. The system of claim 19 wherein the mass spectrometer comprises a quadrupole mass analyzer.

27. The system of claim 19 wherein the mass spectrometer includes an ion trap.

28. The system of claim 19 wherein the analysis results include at least one of:
   results from a acidic liquid chromatography;
   results from a basic liquid chromatography;
   results from a positive ion mass spectrometry;
   results from a negative ion mass spectrometry;
   results from a plurality of samples;
   results from a plurality of separations; and
   results from a plurality of mass spectrometries.

29. The system of claim 19 wherein the separation information comprises at least one of a retention time of a peak and a retention index of a peak.

30. The system of claim 19 wherein the peak information comprises at least one of:
   an intensity of a peak;
   a width of the base of a peak;
   a retention time of the start and end of the base of a peak;
   an intensity of the start and end of the base of a peak;
   a width of a peak at half of the peak's height;
   an area of a peak;
   a symmetry of a peak;
   a noise of a peak;
   a mass associated with a peak;
   a mass-to-charge ratio associated with a peak;

an association of a peak to an entity in an ion tree describing parent-child relationships between ions; and
a list of scans associated with a peak.

31. The system of claim 19 wherein the analysis results include information describing the nature of the analysis results, wherein the information includes at least one of:
a number of primary scans taken during an analysis;
a number of secondary scans taken during an analysis;
a percentage of secondary scans actually taken versus secondary scans that could have been taken;
a number of secondary scans taken that were within the peak of an identified chemical entity;
a percentage of secondary scans taken that were with the peak of an identified chemical entity;
a number of peaks recorded during an analysis;
a number of peaks for which a secondary scan has been taken;
a percentage of peaks for which a secondary scan has been taken;
a number of peaks that have more than one secondary scan associated with it;
a percentage of peaks that have more than one secondary scan associated with it;
an area of the largest peak for which a secondary scan was not performed; and
an area of the smallest peak for which a secondary scan was performed.

32. The system of claim 19 comprising a database for storing at least one of the library of information and the analysis results.

33. The system of claim 19 comparison of the analysis results to a library of information includes comparison of the analysis results to a characteristic of an entity within the library, including a comparison of at least one of:
a retention time of the entity;
a retention index of the entity;
a mass of the entity;
a mass-to-charge ratio for the entity;
a mass of an adduct of the entity;
an isotope relationship of the entity;
a mass of a fragment of the entity;
a relationship of the entity to the entity's child ions;
a relationship of the entity to the entity's parent entity;
relative intensity of the entity;
structural information for the entity;
physical properties of the entity;
a list of physical stocks of the entity;
information available within a public chemical database entry for the entity;
information about the entity available within a second library of information; and
analysis results associated with the entity.

34. The system of claim 19 wherein the library includes information pertaining to at least one of:
a relationship of a parent entity to the entity's child ions;
a relationship of a child entity to the entity's parent entity;
structural information for an entity;
physical properties for an entity;
a list of physical stocks for an entity;
a link to a public chemical database entry for an entity;
a link to a second library of information; and
a link to analysis results associated with an entity.

35. The system of claim 19 wherein the analysis module is configured to display the analysis results and information for an entity that is in the library.

36. The system of claim 19 wherein the analysis module is configured to store, in the library, information about a detected but unidentified chemical entity identified as present in the sample.

37. The system of claim 19 wherein the user interface makes available in human-accessible form at least one of the results of the comparison, information associated with an entity in the library of information, and the determined chemical constituent of the sample.

38. The system of claim 19 wherein the user interface is configured to allow a user of the system to make available in human-accessible form primary mass spectrometry data, select an item of interest from the displayed primary mass spectrometry data, and view information associated with a chemical entity selected from the library of information.

39. The system of claim 38 wherein the chemical entity is selected automatically by the system.

40. The system of claim 38 wherein the chemical entity is selected manually by the user.

41. The system of claim 19 wherein the user interface is configured to allow a user of the system to make available in human-accessible form primary mass spectrometry data, select an item of interest within the primary mass spectrometry data, and make available in human-accessible form the secondary mass spectrometry data associated with the selected item of interest.

42. The system of claim 41 wherein the user interface is configured to make available in human-accessible form an indication that secondary mass spectrometry data associated with the first mass spectrometry data is available.

43. The system of claim 37 wherein the user interface is configured to allow a user of the system to navigate through multiple sets of analysis results data according to the data's hierarchical relationship and to navigate through information associated with entities within the library of information according to the entities' hierarchical relationship.

44. The system of claim 43 wherein the user interface is configured to automatically synchronize the navigation of the analysis results data with the navigation of the information associated with the entities, wherein a change of one causes a change in the other.

45. A computer readable medium having stored thereon computer-executable instructions that when executed by the processor of a computer perform steps comprising:
generating, using a separation technique and a mass spectrometer, separation and mass spectrometry data of a sample, wherein the separation data includes peak information and wherein the mass spectrometry data includes primary and secondary mass spectrometry data;
collecting and storing analysis results, the analysis results including the generated separation and mass spectrometry data;
determining a chemical constituent of the sample by comparison of the analysis results to a library of information indicating characteristics of chemical entities, wherein the comparison is based on the separation and mass spectrometry data, wherein the library of information comprises data generated by the separation technique and mass spectrometer, and wherein the library of information includes separation and mass spectrometry data for identified and unidentified chemical entities; and
making available in human-accessible form an indication of the chemical constituent of the sample.

* * * * *